US006699862B1

(12) United States Patent
Goldstein et al.

(10) Patent No.: US 6,699,862 B1
(45) Date of Patent: *Mar. 2, 2004

(54) INDOLYL-2-PHENYL BISAMIDINES USEFUL AS ANTIPROLIFERATIVE AGENTS

(75) Inventors: Steven W. Goldstein, Noank, CT (US); Banauara L. Mylari, Waterford, CT (US); Jose R. Perez, Salem, CT (US); Edward A. Glazer, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/534,221

(22) Filed: Mar. 24, 2000

Related U.S. Application Data
(60) Provisional application No. 60/136,605, filed on May 27, 1999.

(51) Int. Cl.[7] .................. C07D 403/04; C07D 403/10; A61K 31/4178; A61K 3/506; A61P 17/06
(52) U.S. Cl. .............................. 514/235.2; 514/254.09; 514/256; 514/402; 514/415; 544/143; 544/296; 544/333; 548/312.1; 548/505
(58) Field of Search .............................. 514/235.2, 256, 514/402, 415, 254.09; 544/296, 333, 143; 548/312.1, 505

(56) References Cited

U.S. PATENT DOCUMENTS
6,329,412 B1 * 12/2001 Goldstein et al. ........... 514/385

OTHER PUBLICATIONS
Andrew Streitwieser, Jr. and Clayton H. Heathcock, "Introduction to Organic Chemistry 2nd Ed.", Macmillan New York, 1981, p. 79.*
"Advances in Medicinal Chemistry, vol. 33", Academic Press, 1998, New York, p 151 & 158.*
Aldrich Chemical Company, Milwaukee, WI, 1992, p. 381.*
Tidwell, R. R.; Geratz, J. D.; Dann, O.; Volz, G.; Zeh, D.; Loewe, J. Med. Chem., 21(7), 613–23 (English) 1978.*
Sgorbati, Sergio; Sparvoli, Elio; Levi, Marisa; Chiatante, Donato, Physiol. Plant., 75(4), 479–84 (English) 1989.*
Bestor, et al., Proc. Nat. Acad. Sci., 80, pp. 5559–5563 (1983).
Li, et al., Cell, 69, pp. 915–926 (1992).
Shen, et al., Cell, 71, pp. 1073–1080 (1992).
Laird, et al., Cell, 81, pp. 197–205 (1995).
Schroeder, et al., Biochem. & Biophys. Res. Comm., 235, pp. 403–406 (1997).

* cited by examiner

Primary Examiner—Mukund J. Shah
Assistant Examiner—Thomas McKenzie
(74) Attorney, Agent, or Firm—Peter C. Richardson; Paul H. Ginsburg; Krishna G. Banerjee

(57) ABSTRACT

Novel indolyl-2-phenyl bisamidines are described which are DNA methyltransferase inhibiting agents, and pharmaceutical compositions containing them are used as antiproliferative agents for treating a disease, especially a neoplastic disease, characterized by abnormally rapid proliferation of tissue involved in said disease; said indolyl-2-phenyl bisamidines comprising a

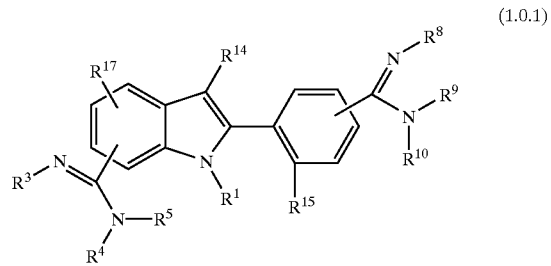

(1.0.1)

and a pharmaceutically acceptable salt thereof, wherein:
$R^1$ is hydrogen or $(C_1-C_3)$alkyl; $R^3$, $R^4$, $R^5$, $R^8$, $R^9$, and $R^{10}$ are hydrogen or $(C_1-C_3)$alkyl, or $R^3$ and $R^4$ may be taken together, or $R^8$ and $R^9$ may be taken together with the nitrogen atoms to which they are attached, to form an imidazolinyl group; $R^{14}$ is —H; —NHC(=O)$(CH_2)_m R^{20}$; —$(CH_2)_m R^{20}$; —CH$(CH_3)R^{20}$; —$(CH_2)_m$$(C_6H_3)$—$R^{17}$; —$(CH_2)_m(C_6H_3)$—$R^{20}$; —$(CH_2)_m$(heterocyclyl)—$R^{17}$; —$(CH_2)_m$(heterocyclyl)—$R^{20}$; —$CH_2$CH=CHR$^{20}$; —$(CH_2)_m$C(=O)NH—CHR$^{20}R^{21}$; or —$(CH_2)_m$C(=O)NH—CH$_2$—C(=O)NHCHR$^{20}R^{21}$; where $R^{17}$ is hydrogen; halogen; $(C_1-C_3)$alkyl; —CF$_3$; —CN; —NO$_2$; —N$(R^1)_2$; —OH; or $(C_1-C_3)$ alkyl$(C_1-C_3)$alkoxy; $R^{21}$ is —C(=O)OR$^1$; CH(OH)CH$_2$OH; —C(=O)NH$_2$; or —C(=O)H; $R^{21}$ is hydrogen; $(C_1-C_6)$alkyl; —$(CH_2)_n$R$^{22}$; —CH(CH$_3$)CH$_2$C(=O)OR$^1$; and —CH$_2$—$(C_6H_5)$; and R$^{22}$ is —H; —NH$_2$; —OR$^1$; —SR$^1$; —CN; —OCH$_2$—$(C_6H_5)$; —O(CH$_2)_m$—OR$^1$; —C(=O)OR$^1$; thienyl; tetrahydropyranyl; —CH(OH)CH$_2$OH; —C(=O)C(CH$_3$)=CH$_2$; —NHC(=O)OCH$_2$—$(C_6H_5)$; and —S(=O)$_2$R$^1$; where m is 1, 2, or 3; and n is 1 through 5, inclusive.

12 Claims, No Drawings

INDOLYL-2-PHENYL BISAMIDINES USEFUL AS ANTIPROLIFERATIVE AGENTS

REFERENCE TO RELATED APPLICATIONS

This application is a continuation of U.S. Provisional Application Serial No. 60/136,605 filed on May 27, 1999 and now abandoned, the benefit of the filing date of which is hereby claimed.

Reference is made to U.S. application Ser. No. 09/535,359 filed on Mar. 24, 2000 and now U.S. Pat. No. 6,329,412 B1, which is a continuation of U.S. Provisional Application Serial No. 60/136,606 filed on May 27, 1999 and now abandoned.

BACKGROUND OF THE INVENTION

The present invention is concerned with novel compounds which are biologically active as inhibitors of the DNA methyltransferase enzyme and consequently useful in the treatment of diseases and conditions which involve unregulated differentiation of cells and cellular processes. The DNA methyltransferase enzyme (EC 2.1.1.37) catalyzes the covalent methylation of the DNA base cytosine at the C5 position of that base. This modification of the base cytosine in a DNA molecule has been shown to play a vital role in the transcriptional inactivation, i.e., silencing of the chromatin as well as in the development and differentiation of cells. The resulting unregulated differentiation of cells and cellular processes is found to be a contributing factor in the development via transformation, and growth of particular cancers and malignancies. The compounds of the present invention hinder the occurrence of the just-described biochemical process and constrain its pathogenic sequelae. As a result, the compounds of Formula (1.0.0) are useful as chemopreventative and chemotherapeutic agents for treating cancers, proliferative diseases such as psoriasis, and hyperplasia.

DESCRIPTION OF THE STATE OF THE ART

The DNA methyltransferase enzyme (EC 2.1.1.37), which has been identified as a single gene product of 190 Kd, catalyzes the cofactor S-adenosylmethionine (SAM) dependent methylation of the cytosine base at the C5 carbon of the pyrimidine base. See, e.g., T. H. Bestor and V. M. Ingram, *Proc. Nat. Acad. Sci.*, 80:5559–5563 (1983). This DNA modification has been shown to play a vital role in the transcriptional inactivation, i.e., silencing of the chromatin, as well as in the development and differentiation of cells, as described in more detail in E. Li, T. H. Bestor and R. Jaenisch, *Cell*, 69:915–926 (1992).

It is important to point out that aberrant changes in DNA methylation patterns as well as DNA methyltransferase activity itself have been implicated in the progression of cancer. There are two proposed mechanisms by which DNA methyltransferase has been correlated with this progression. (A) The first proposed mechanism is the hypermethylation/hypomethylation of key cell cycle regulatory genes and oncogenes including P16, P15, c-myc and P53. See, e.g., M. Schroeder and Mass, M. J., Biochem.& *Biophys. Res. Comm.*, 235:403–406 (1997). (B) The second proposed mechanism is the low frequency DNA methyltransferase mediated deamination of the cytosine base causing a cytosine to thymine point mutation in the DNA sequence. See, e.g., J. -C. Shen, W. M. Rideout III and P. A. Jones, *Cell*, 71:1073–1080 (1992).

Further work in the art also supports the correlation between DNA methyltransferase activity and the transformation and progression of colon cells to malignant carcinomas in min-/APC (−/−) knock-out mice, as described in more detail in P. W. Laird, L. Jackson-Grusby, A. Fazell, S. L. Dickinson, W. E. Jung,. E. Li, R. A. Wienberg and R. Jaenisch, *Cell*, 81:197–205 (1995).

SUMMARY OF THE INVENTION

The present invention relates to heterocyclic bisamidines useful as antiproliferative agents, comprising a compound of Formula (1.0.0):

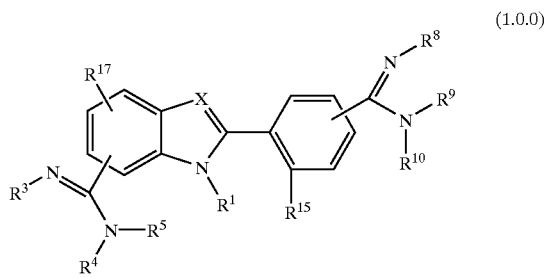

(1.0.0)

and a pharmaceutically acceptable salt thereof, wherein:

x is —C($R^{14}$)—; or —N—;

$R^1$ is independently selected from the group consisting of hydrogen; and ($C_1$–$C_3$)alkyl;

$R^3$, $R^4$, $R^5$, $R^8$, $R^9$, and $R^{10}$ are each independently selected from the group consisting of hydrogen; and ($C_1$–$C_3$)alkyl;

—or—

$R^3$ and $R^4$ may be taken together, or $R^8$ and $R^9$ may be taken together with the nitrogen atoms to which they are attached, to form an imidazolinyl group; or further together with an additional ring carbon, —$CH_2$—, to form a 1,4,5,6-tetrahydropyrimidinyl group;

$R^{14}$ is independently selected from the group consisting of —H; —NHC(=O)($CH_2$)$_m$$R^{20}$; —($CH_2$)$_m$$R^{20}$; —CH($CH_3$)$R^{20}$; —($CH_2$)$_m$($C_6H_3$)—$R^{17}$; —($CH_2$)$_m$($C_6H_3$)—$R^{20}$; —($CH_2$)$_m$(heterocyclyl)—$R^{17}$; —($CH_2$)$_m$(heterocyclyl)—$R^{20}$; —$CH_2$CH=CH$R^{20}$; —($CH_2$)$_m$C(=O)NHCH$R^{20}R^{21}$; and —($CH_2$)$_m$C(=O)NH—$CH_2$—C(=O)NHCH$R^{20}R^{21}$;

$R^{15}$ is independently selected from the group consisting of hydrogen; —$OR^1$; —O—($C_1$–$C_3$) alkylenyl-$R^{20}$; and —$OR^{20}$;

$R^{17}$ is independently selected from the group consisting of hydrogen; halogen; ($C_1$–$C_3$)alkyl; —$CF_3$; —CN; —$NO_2$; —N($R^1$)$_2$; —OH; and ($C_1$–$C_3$) alkyl($C_1$–$C_3$) alkoxy;

$R^{20}$ is independently selected from the group consisting of —C(=O)$OR^1$; CH(OH)$CH_2$OH; —C(=O)$NH_2$; and —C(=O)H;

$R^{21}$ is independently selected from the group consisting of hydrogen; ($C_1$–$C_6$)alkyl; —($CH_2$)$_n$$R^{22}$; —CH($CH_3$)$CH_2$C(=O)$OR^1$; and —$CH_2$—($C_6H_5$);

$R^{22}$ is independently selected from the group consisting of —H; —$NH_2$; —$OR^1$; —$SR^1$; —CN; —$OCH_2$—($C_6H_5$); —O($CH_2$)$_m$—$OR^1$; —C(=O)$OR^1$; thienyl; tetrahydropyranyl; —CH(OH)$CH_2$OH; —C(=O)C($CH_3$)=$CH_2$; —NHC(=O)$OCH_2$—($C_6H_5$); and —S(=O)$_2$$R^1$;

m is an integer independently selected from 1, 2, and 3; and n is an integer independently selected from 1 through 5, inclusive.

The present invention further relates to a pharmaceutical composition for use as an antiproliferative agent, comprising a therapeutically effective amount of a heterocyclic bisamidine compound of Formula (1.0.0) as above described, together with a pharmaceutically acceptable carrier for said compound. The present invention relates as well to a corresponding method of treating a neoplastic or a non-neoplastic disease characterized by abnormally rapid proliferation of tissue involved in said disease, comprising administering to a patient in need of such treatment a therapeutically effective amount of a compound of Formula (1.0.0) as above described. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *Pneumocystis carinii* infection, and restenosis.

The present invention still further relates to a pharmaceutical composition for use as a DNA methyltransferase inhibiting agent, comprising a therapeutically effective amount of a heterocyclic bisamidine compound of Formula (1.0.0) as above described, together with a pharmaceutically acceptable carrier for said compound. The present invention relates as well to a corresponding method of treating a neoplastic or a non-neoplastic disease characterized by abnormally rapid proliferation of tissue involved in said disease which is mediated by or associated with abnormally increased levels of DNA methylation, comprising administering to a patient in need of such treatment a therapeutically effective amount of a compound of Formula (1.0.0) as above described. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *Pneumocystis carinii* infection, and restenosis.

Antineoplastic and antiproliferative agents of the present invention may also be used in the therapy of psoriasis, a non-neoplastic disease of the skin characterized by abnormally rapid proliferation of epidermal cells, as well as for the beneficial treatment of *Pneumocystis carinii*. Therapeutic agents of the present invention are useful in the treatment of proliferative diseases such as restenosis, in addition to cancer and psoriasis.

DETAILED DESCRIPTION OF THE INVENTION

The present invention is concerned with novel compositions of matter which are heterocyclic bisamidines useful as antiproliferative agents, comprising a compound of Formula (1.0.0):

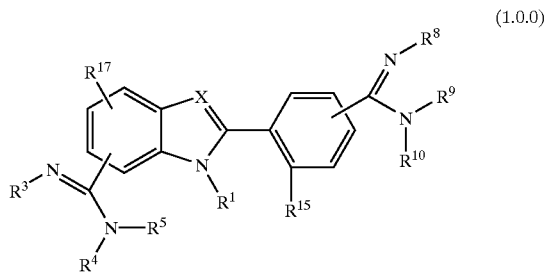

and a pharmaceutically acceptable salt thereof.

The X moiety of the compounds of Formula (1.0.0) has the meaning —C($R^{14}$)— or —N—. Accordingly, there results an indolyl-2-phenyl moiety with a 3-position substituent $R^{14}$ as the nucleus of the compounds of Formula (1.0.0) when X has the meaning —C($R^{14}$)—; and a benzimidazolinyl-2-phenyl moiety as the nucleus of the compounds of Formula (1.0.0) when X has the meaning —N—. Where $R^{14}$ has the meaning of hydrogen, then the resulting nucleus is essentially unsubstituted at the 3-position. These basic nuclei may be represented by partial Formulas (1.1.0) and (1.2.0) as follows:

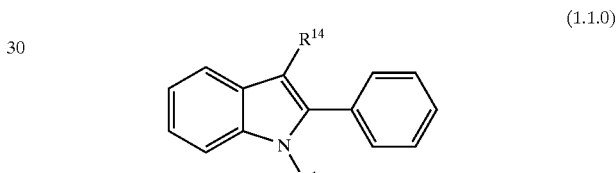

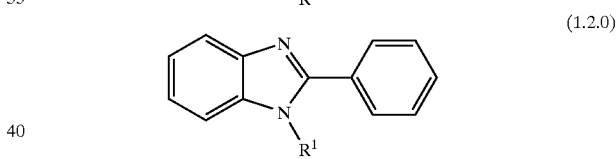

Of the two above-depicted nuclei, the indolyl-2-phenyl-3-$R^{14}$ moiety of Formula (1.1.0) is preferred.

The $R^1$ substituent attached to the 1-position nitrogen atom of either the indolyl-2-phenyl or benzimidazolinyl-2-phenyl nucleus has the meaning of hydrogen or ($C_1$–$C_3$) alkyl, with hydrogen and methyl being the preferred meanings.

As used herein, the term "alkyl", e.g., "($C_1$–$C_3$) alkyl", is intended to have the meaning of a straight or branched chain alkyl group having the indicated number of carbon atoms. Thus, in the case of "($C_1$–$C_3$) alkyl" the intended meaning includes methyl, ethyl, n-propyl, and iso-propyl.

The compounds of Formula (1.0.0) are further characterized by having a carbamimidoyl group attached to both the indolyl or benzimidazolinyl component of the basic nucleus, as well as to the phenyl component of said nucleus. These carbamimidoyl groups may be attached to various carbon atoms of said components. The following configurations are representative of some, but not all of the possible configurations included within the scope of the present invention, as illustrated by partial Formulas (1.3.1) through (1.3.12), inclusive:

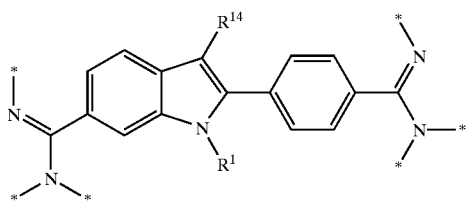
(1.3.1)
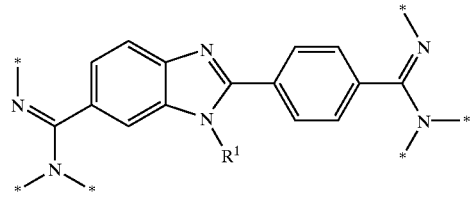
(1.3.7)
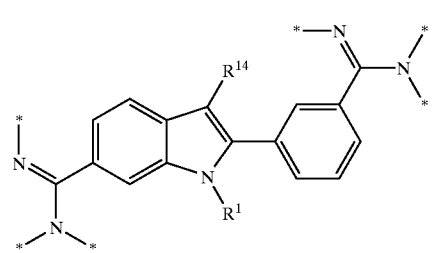
(1.3.2)
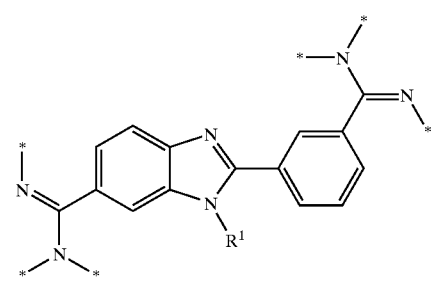
(1.3.8)
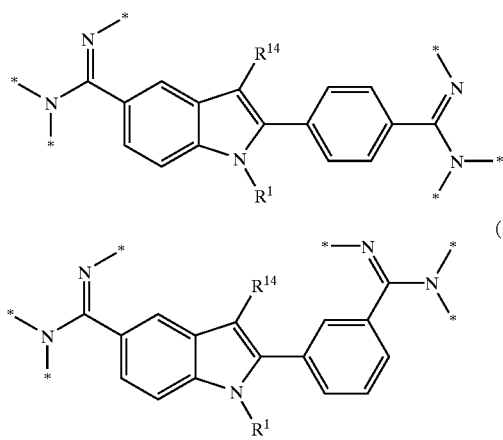
(1.3.3)
(1.3.4)
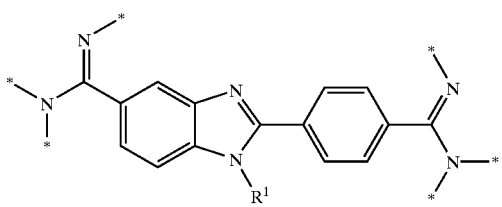
(1.3.9)
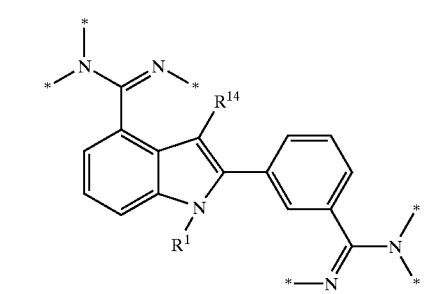
(1.3.5)
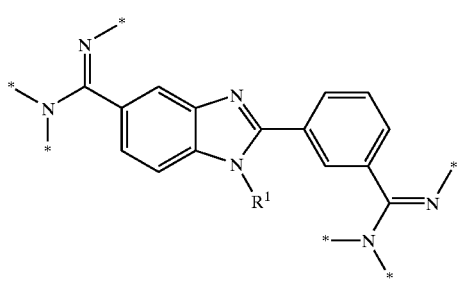
(1.3.10)
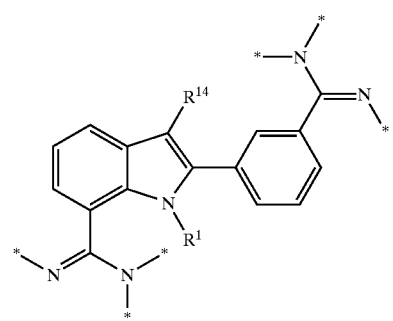
(1.3.6)
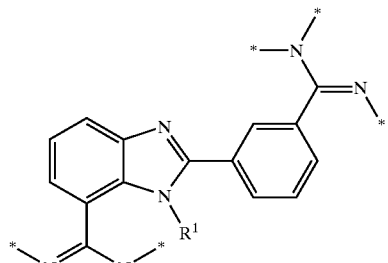
(1.3.11)

(1.3.12)

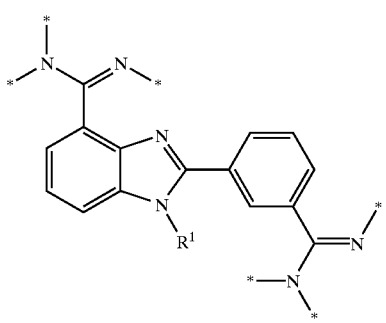

where the symbol "*" indicates the points of attachment of the substituents $R^3$, $R^4$, $R^5$, $R^8$, $R^9$, and $R^{10}$, which are not shown in order to simplify the illustration.

Of the above-depicted configurations, those of partial Formulas (1.3.1) and (1.3.10) are preferred, and that of partial Formula (1.3.1) is most preferred.

The substituents on the carbamimidoyl groups illustrated in partial Formulas (1.3.1) through (1.3.16) above are designated $R^3$, $R^4$, $R^5$, $R^8$, $R^9$, and $R^{10}$ and in one embodiment they are each independently selected from the group consisting of hydrogen and $(C_1–C_3)$ alkyl. In this embodiment, accordingly, the carbamimidoyl substituents on the indolyl-2-phenyl and benzimidazolinyl-2-phenyl nuclei are selected from the following group illustrated by partial Formulas (1.4.1) through (1.4.15), inclusive:

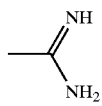
(1.4.1)

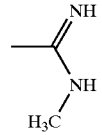
(1.4.2)

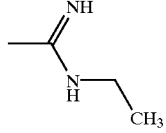
(1.4.3)

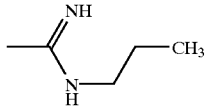
(1.4.4)

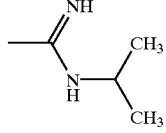
(1.4.5)

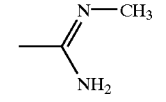
(1.4.6)

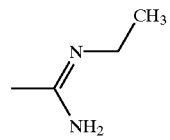
(1.4.7)

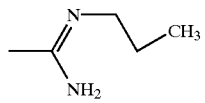
(1.4.8)

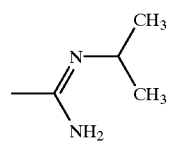
(1.4.9)

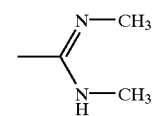
(1.4.10)

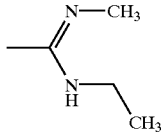
(1.4.11)

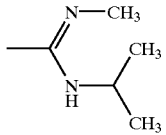
(1.4.12)

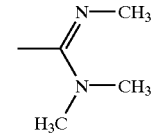
(1.4.13)

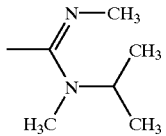
(1.4.14)

(1.4.15)

Of the above-described carbamimidoyl moieties, the preferred embodiments are those of partial Formulas (1.4.1), (1.4.2), (1.4.5), (1.4.6), (1.4.9), (1.4.10), and (1.4.13). Of these, the more preferred embodiments are those of partial Formulas (1.4.1), (1.4.5), (1.4.9), and (1.4.10). Of these, the most preferred embodiments are those of partial Formulas (1.4.1), (1.4.5), and (1.4.10).

In another embodiment of the compounds of Formula (1.0.0), $R^3$ and $R^4$ may be taken together, or $R^8$ and $R^9$ may be taken together, with the nitrogen atoms to which they are attached, to form an imidazolinyl group; or further together with an additional ring carbon, —CH$_2$—, to form a 1,4,5, 6-tetrahydropyrimidinyl group. These embodiments may be illustrated by the following partial Formulas (1.5.1) through (1.5.4):

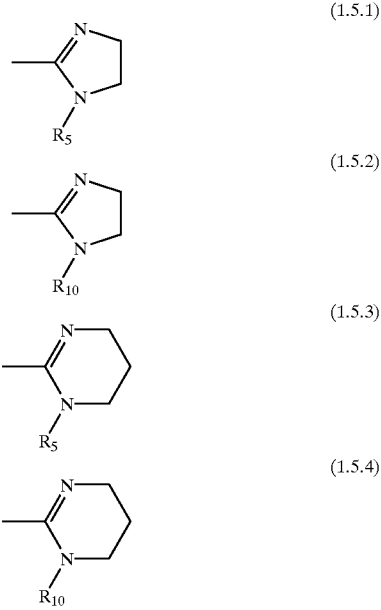

where R$^5$ and R have the same meaning as set out further above.

R$^{14}$ is the substituent which is present on the 3-position carbon atom of the indolyl-2-phenyl nucleus of partial Formula (1.1.0), or on the 3-position nitrogen atom of the benzimidazolinyl-2-phenyl nucleus of partial Formula (1.2.0). R$^{14}$ is the most important and the most variable in structure of all of the substituents which appear on the compounds of Formula (1.0.0). It is hypothesized that the R$^{14}$ substituent plays a key role in determining the DNA methyltransferase inhibiting activity of the compounds of Formula (1.0.0). R$^{14}$ is independently selected from the group consisting of —H; —NHC(=O)(CH$_2$)$_m$R$^{20}$; —(CH$_2$)$_m$ R$^{20}$; —CH(CH$_3$)R$^{20}$; —(CH$_2$)$_m$(C$_6$H$_3$)—R$^{17}$; —(CH$_2$)$_m$(C$_6$H$_3$)—R$^{20}$; —(CH$_2$)$_m$(heterocycly)—R$^{17}$; —(CH$_2$)$_m$(heterocyclyl)—R$^{20}$; —CH$_2$CH=CHR$^{20}$; —(CH$_2$)$_m$C(=O)NHCHR$^{20}$R$^{21}$; and —(CH$_2$)$_m$C(=O)NH—CH$_2$—C(=O)NHCHR$^{20}$R$^{21}$.

As used herein, the term "heterocyclyl" is intended to have the meaning of an aromatic or non-aromatic, monocyclic or bicyclic, 3- to 10-membered carbocyclic ring system in which at least one of the carbon atoms of the ring has been replaced by a heteroatom independently selected from N, O and S. Preferably two, and more preferably one heteroatom is present, except that in the case of nitrogen, as many as four N heteroatoms may be present. The heterocyclyl group may comprise one or two fused rings, and further may include a combination of a saturated heterocyclic ring and a non-heterocyclic aryl-fused ring.

In prefered embodiments of the present invention where "heterocyclyl" refers to a non-aromatic mono-cyclic ring system, its meaning includes, but is not limited to, a member selected from the group consisting of oxiranyl, pyrrolidinyl, pyrazolidinyl, imidazolidinyl, tetrazolidinyl, piperidinyl, piperazinyl, morpholinyl, thiomorpholinyl, and benzodioxolane, especially 1,3-benzodioxol-5-yl. In more preferred embodiments of this type, "heterocyclyl" has the meaning pyrrolidinyl, piperidinyl, piperazinyl, or morpholinyl.

The term "heterocyclyl" also refers to an aromatic mono- or bicyclic ring system comprising a 5- or 6-membered ring containing from 1 to 4 heteroatoms independently selected from N, O, and S, optionally having a 3- or 4-carbon chain attached to adjacent carbons thereof to form a fused 9- or 10-membered aromatic ring system. In preferred embodiments of the present invention where the term "heterocyclyl" refers to mono- or bicyclic aromatic ring systems, its meaning includes, but is not limited to, furyl, thienyl, pyrrolyl, oxazolyl, isoxazolyl, thiazolyl, imidazolyl, pyridyl, pyrazinyl, pyrazolyl, pyrimidinyl, oxadiazolyl, thiadiazolyl, parathiazinyl, indolyl, benzo[b]furanyl, benzimidazolyl, benzthiazolyl, quinolinyl, and isoquinolinyl. In more preferred embodiments of this type, "heterocyclyl" has the meaning of pyrrolyl, imidazolyl, oxazolyl or indolyl.

With regard to all of the above-described meanings of "heterocyclyl", in the more preferred embodiments of the present invention, it has the meaning of pyrrolyl, pyrrolidinyl, imidazolyl, oxazolyl, piperidinyl, piperazinyl, morpholinyl, or indolyl.

In the definitions of the R$^{14}$ moiety, the heterocyclyl group is contained in the definitions: —(CH$_2$)$_m$(heterocyclyi)—R$^{17}$ and —(CH$_2$)$_m$(heterocyclyl)—R$^{20}$, where m is an integer independently selected from 1, 2, and 3. Accordingly, it will be appreciated that where a heterocyclyl group is attached to the basic nucleus of a compound of Formula (1.0.0), it will be by means of an alkyleneyl bridge. In preferred embodiments, the alkyleneyl bridge will be methylene.

In addition to the above-mentioned heterocyclyl groups defining the R$^{14}$ moiety, there is also the meaning of the phenyl groups contained in the definitions: —(CH$_2$)$_m$(C$_6$H$_3$)—R$^{17}$ and —(CH$_2$)$_m$(C$_6$H$_3$)—R$^{20}$. As in the case of the heterocyclyl groups, the phenyl groups are also attached to the basic nucleus of a compound of Formula (1.0.0) by means of an alkyleneyl bridge which is preferably methylene.

Both the heterocyclyl and phenyl groups defining the R$^{14}$ moiety are substituted by a group defined by R$^{17}$ or by a group defined by R$^{20}$. The R$^{17}$ group comprises a member independently selected from the group consisting of hydrogen; halogen; (C$_1$–C$_3$)alkyl; —CF$_3$; —CN; —NO$_2$; —N(R$^1$)$_2$; —OH; and (C$_1$–C$_3$) alkyl(C$_1$–C$_3$) alkoxy. The R$^{17}$ group also defines the substituents from which a member is selected for any given available position of the benzo-portion of the basic nucleus of a compound of Formula (1.0.0), which comprises a benzo-fused ring system consisting of an indolyl-2-phenyl moiety or a benzimidazolinyl-2-phenyl moiety.

Accordingly, it will be appreciated that the same group of substituents is available for selection with respect to the benzo-portion of the basic nucleus, as it is with respect to a phenyl or heterocycl group attached at the 3-position of said basic nucleus, i.e., the 3-position of the indolyl-2-phenyl moiety or the benzimidazolinyl-2-phenyl moiety. Thus, preferred embodiments of the compounds of Formula (1.0.0) which have incorporated therein different substituent groups of the type just mentioned are illustrated in the following partial Formulas (1.6.1) through (1.6.6), inclusive:

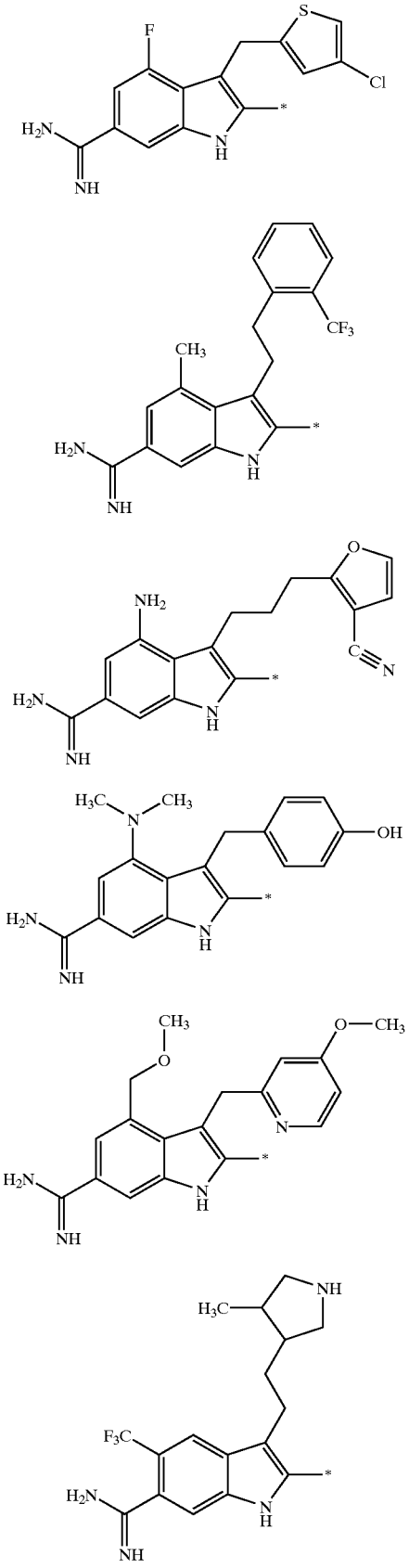

(1.6.1)
(1.6.2)
(1.6.3)
(1.6.4)
(1.6.5)
(1.6.6)

The $R^{14}$ substituent group may also have the meaning of —NHC($=$O)(CH$_2$)$_m$R$^{20}$, where m is 1, 2 or 3. Accordingly, $R^{14}$ includes but is not limited to representative moieties of partial Formulas (1.6.10) through (1.6.13), inclusive:

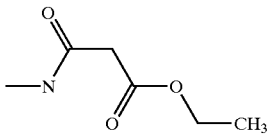

(1.6.10)

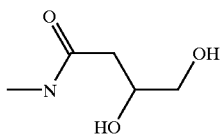

(1.6.11)

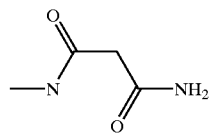

(1.6.12)

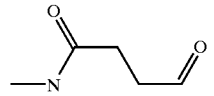

(1.6.13)

Further, the $R^{14}$ substituent group may also have the meaning of an $R^{20}$ substituent group connected by way of an alkylene or alkenylene bridge, defined as —(CH$_2$)$_m$R$^{20}$, where m is 1, 2 or 3; —CH(CH$_3$)R$^{20}$; or CH$_2$CH$=$CHR$^{20}$. Accordingly, $R^{14}$ includes but is not limited to representative moieties of partial Formulas (1.6.20) through (1.6.29), inclusive:

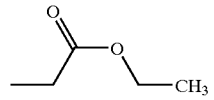

(1.6.20)

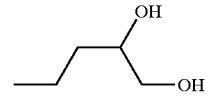

(1.6.21)

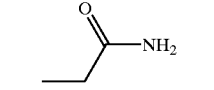

(1.6.22)

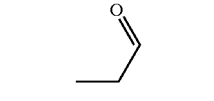

(1.6.23)

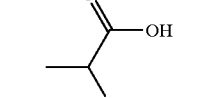

(1.6.24)

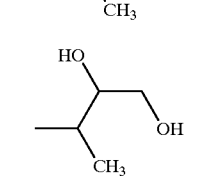

(1.6.25)

(1.6.26) 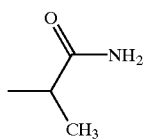

(1.2.27) 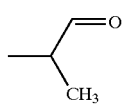

(1.6.28) 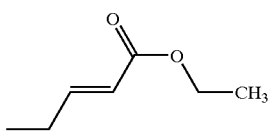

(1.6.29) 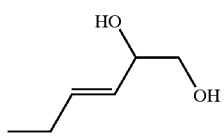

The $R^{14}$ substituent group may further have the meaning of an $R^{20}$ and an $R^{21}$ substituent group connected by way of specific moieties defined as $(CH_2)_mC(=O)NHCHR^{20}R^{21}$ and $—(CH_2)_mC(=O)NH—CH_2—C(=O)NHCHR^{20}R^{21}$. Accordingly, $R^{14}$ includes but is not limited to representative moieties of partial Formulas (1.6.30) through (1.6.33), inclusive:

(1.6.30) 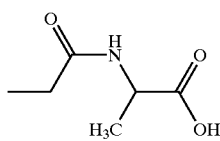

(1.6.31) 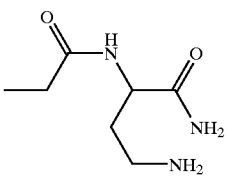

(1.6.32) 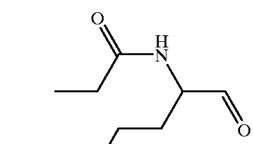

(1.6.33) 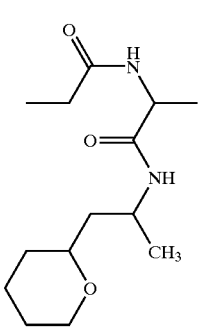

The $R^{15}$ group is attached as a substituent at the 2-position of the phenyl component of the indolyl-2-phenyl or benzimidazolinyl-2-phenyl basic nucleus. The $R^{15}$ substituent is a member independently selected from the group consisting of hydrogen; $—OR^1$; $—O—(C_1-C_3)$alkylenyl-$R^{20}$; and $—OR^{20}$. The $R^{20}$ substituent, in turn, is a member independently selected from the group consisting of $—C(=O)OR^1$, $CH(OH)CH_2OH$, $—C(=O)NH_2$, and $—C(=O)H$; where the $R^{21}$ substituent is a member independently selected from the group consisting of hydrogen, $(C_1-C_6)$ alkyl, $—(CH_2)_nR^{22}$ where n is an integer independently selected from 1 through 5 inclusive, $—CH(CH_3)$ $CH_2C(=O)OR^1$, and $—CH_2—(C_6H_5)$.

The $R^{22}$ substituent, which appears in the definition of the $R^{21}$ substituent group described above, is independently selected from the group consisting of $—NH_2$, $—OR^1$, $—SR^1$, $—CN$, $—OCH_2—(C_6H_5)$, $—O(CH_2)_m—OR^1$, $—C(=O)OR^1$, thienyl, tetrahydropyranyl, $—CH(OH)$ $CH_2OH$, $—C(=O)C(CH_3)=CH_2$, $—NHC(=O)OCH_2—$ $(C_6H_5)$, and $—S(=O)_2R^1$.

Consequently, taking into consideration all of the above-described substituent definitions, the $R^{15}$ substituent groups include, but are not limited to, the following examples illustrated in partial Formulas (1.7.1) through (1.7.10) inclusive:

(1.7.1) —OH (1.7.2) —OCH$_3$ (1.7.3) 

(1.7.4) 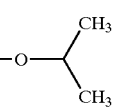

(1.7.5) 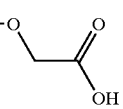

(1.7.6) 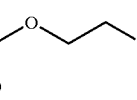

(1.7.7) 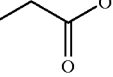

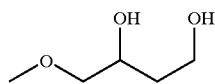

(1.7.8)

(1.7.9)

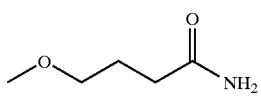

(1.7.10)

The above description contains an indication of subgeneric areas within the scope of the compounds of Formula (1.0.0) which are preferred. There are also a number of specific embodiments within the scope of the compounds of Formula (1.0.0) which are preferred aspects of the present invention. These specific embodiments include but are not limited to those illustrated in the following Formulas (2.0.0) through (2.0.61) inclusive:

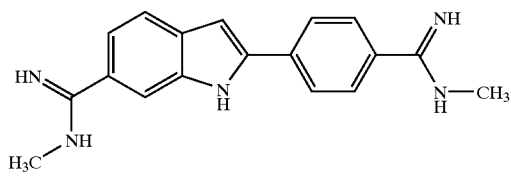

(2.0.0)

N-Methyl-2-[4-(N-methylcarbamimidoyl)-phenyl]-1H-indole-6-carboxamidine dihydrochloride

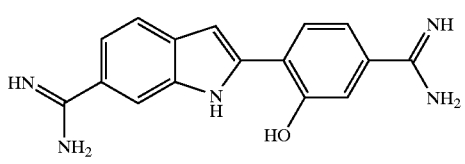

(2.0.1)

2-[4-(Carbamimidoyl-2-hydroxy-phenyl)-1H-indole-6-carboxamidine dihydrochloride

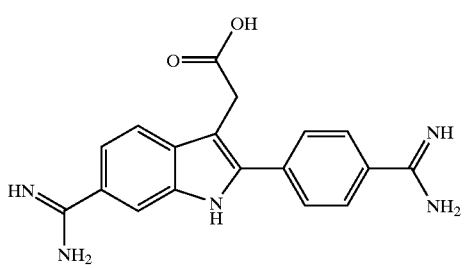

(2.0.2)

[6-Carbamimidoyl-2-(4-carbamimidoyl-phenyl)-1H-indol-3-yl]-acetic acid dihydrochloride

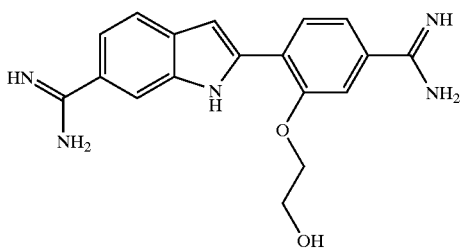

(2.0.3)

2-[4-Carbamimidoyl-2-(2-hydroxy-ethoxy)-phenyl]-1H-indole-6-carboxamidine dihydrochloride

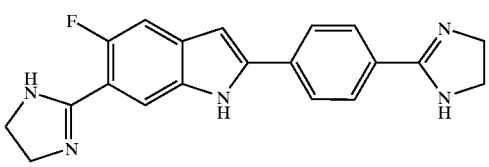

(2.0.4)

6-(4,5-Dihydro-1H-imidazol-2-yl)-2-[4-(4,5-dihydro-1H-imidazol-2-yl)-phenyl]-5-fluoro-1H-indole dihydrochloride (2.0.5)

2-(4-Carbamimidoyl-2-methoxy-phenyl)-1H-indole-6-carboxamidine dihydrochloride

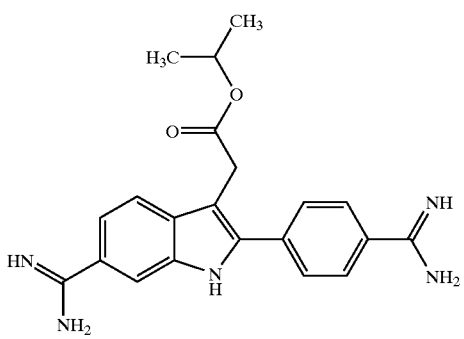

(2.0.6)

[6-Carbamimidoyl-2-(4-carbamimidoyl-phenyl)-1H-indol-3-yl]acetic acid isopropyl ester dihydrochloride (2.0.7)

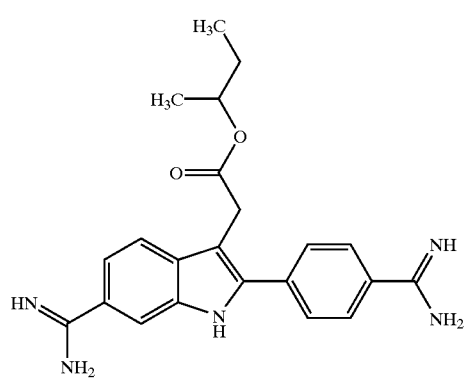

[6-Carbamimidoyl-2-(4-carbamimidoyl-phenyl)-1H-indol-3-yl]acetic acid sec-butyl ester dihydrochloride (2.0.8)

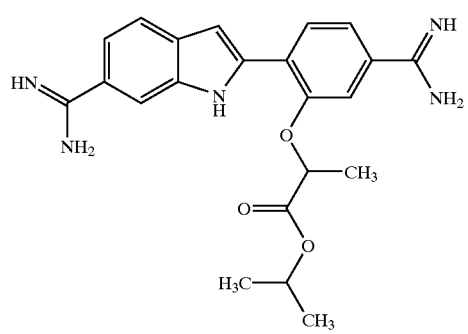

2-[5-Carbamimidoyl-2-(6-carbamimidoyl-1H-indol-2-yl)phenoxy]-propionic acid isopropyl ester dihydrochloride (2.0.9)

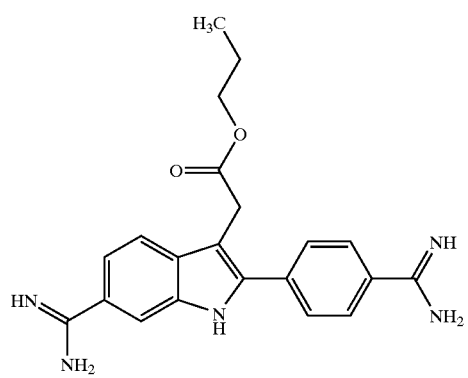

[6-Carbamimidoyl-2-(4-carbamimidoyl-phenyl)-1H-indol-3-yl]-acetic acid propyl ester dihydrochloride (2.0.10)

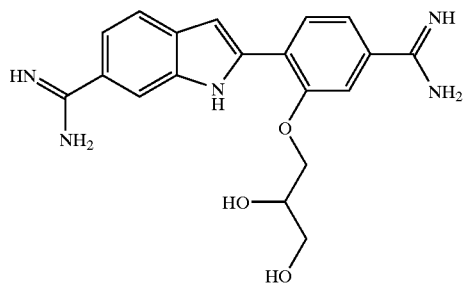

2-[4-Carbamimidoyl-2-(2,3-dihydroxy-propoxy)-phenyl]-1H-indole-6-carboxamidine dihydrochloride (2.0.11)

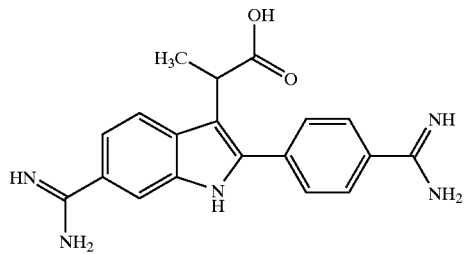

2-[6-Carbamimidoyl-2-(4-carbamimidoyl-phenyl)-1H-indol-3-yl]-propionic acid dihydrochloride (2.0.12)

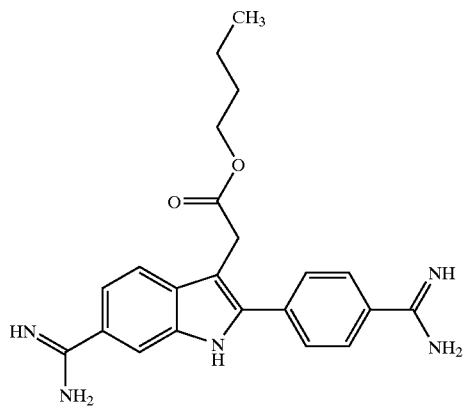

[6-Carbamimidoyl-2-(4-carbamimidoyl-phenyl)-1H-indol-3-yl]-acetic acid butyl ester dihydrochloride (2.0.13)

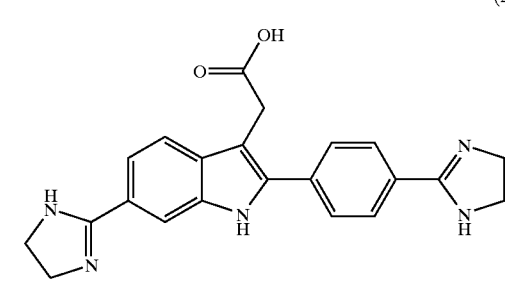

{6-(4,5-Dihydro-1H-imidazol-2-yl)-2-[4-(4,5-dihydro-1H-imidazol-2-yl)-phenyl]-1H-indol-3-yl}-acetic acid dihydrochloride (2.0.14)

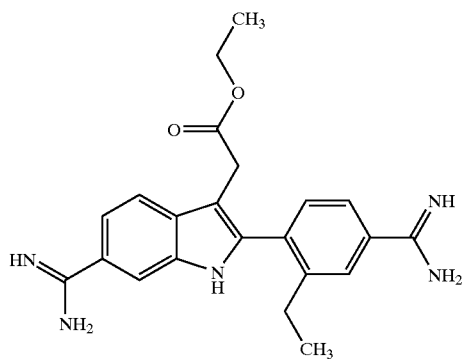

[6-Carbamimidoyl-2-(4-carbamimidoyl-2-
methoxy-phenyl)-1H-indol-3-yl]-acetic acid
ethyl ester dihydrochloride (2.0.15)

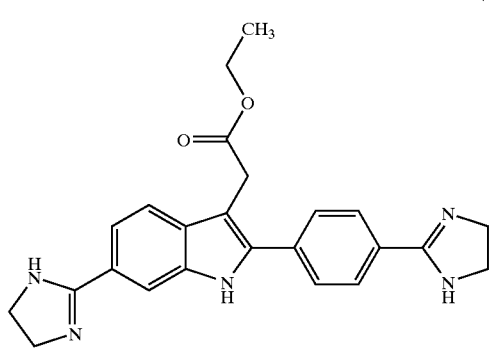

{6-(4,5-Dihydro-1H-imidazol-2-yl)-2-[4-(4,5-
dihydro-1H-imidazol-2-yl)-phenyl]-1H-indol-3-
yl}-acetic acid ethyl ester dihydrochloride (2.0.16)

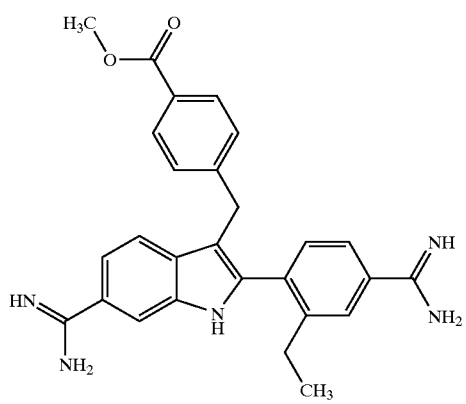

4-[6-Carbamimidoyl-2-(4-carbamimidoyl-
phenyl)-1H-indol-3-ylmethyl]-benzoic acid
methyl ester dihydrochloride (2.0.17)

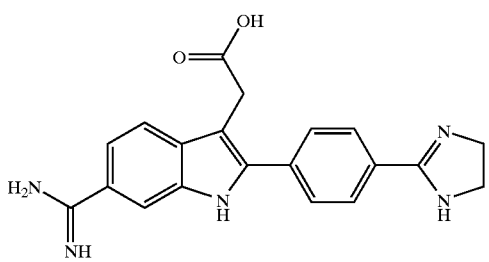

[6-Carbamimidoyl-2-(4-carbamimidoyl-2-
methoxy-phenyl)-1H-indol-3-yl]-acetic acid
ethyl ester dihydrochloride (2.0.18)

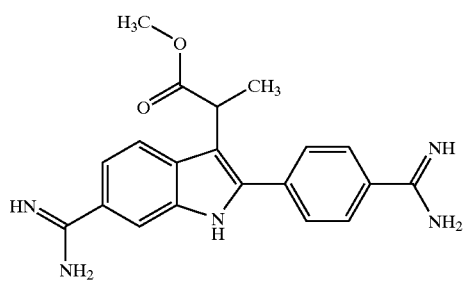

2-[6-Carbamimidoyl-2-(4-carbamimidoyl-
phenyl)-1H-indol-3-yl]-propionic acid methyl
ester dihydrochloride (2.0.19)

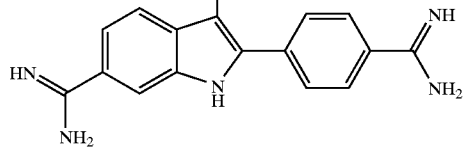

5-[6-Carbamimidoyl-2-(4-carbamimidoyl-
phenyl)-1H-indol-3-ylmethyl]-furan-2-
carboxylic acid methyl ester dihydrochloride (2.0.20)

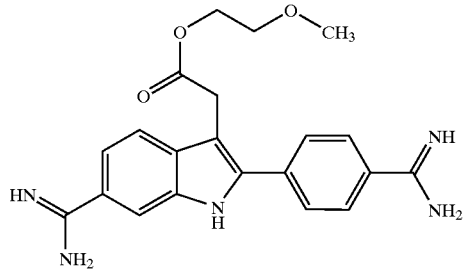

[6-Carbamimidoyl-2-(4-carbamimidoyl-
phenyl)-1H-indol-3-yl]-acetic acid 2-methoxy-
ethyl ester dihydrochloride (2.0.21)

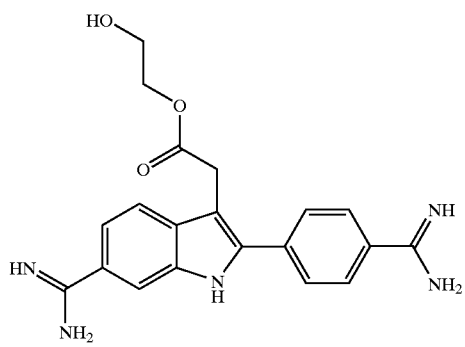

[6-Carbamimidoyl-2-(4-carbamimidoyl-phenyl)-1H-indol-3-yl]-acetic acid 2-hydroxy-ethyl ester dihydrochloride (2.0.22)

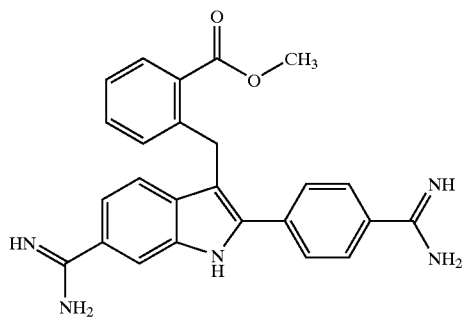

2-[6-Carbamimidoyl-2-(4-carbamimidoyl-phenyl)-1H-indol-3-ylmethyl]-benzoic acid methyl ester dihydrochloride (2.0.23)

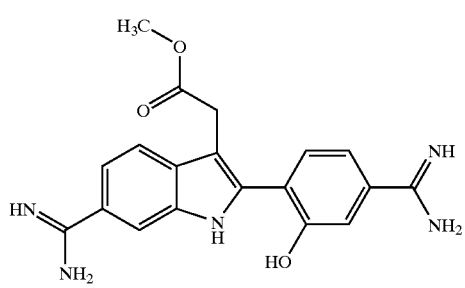

[6-Carbamimidoyl-2-(4-carbamimidoyl-2-hydroxy-phenyl)-1H-indol-3-yl]-acetic acid methyl ester dihydrochloride (2.0.24)

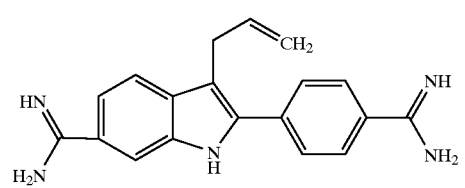

2-(4-Carbamimidoyl-phenyl)3-allyl-1H-indole-6-carboxamidine dihydrochloride (2.0.25)

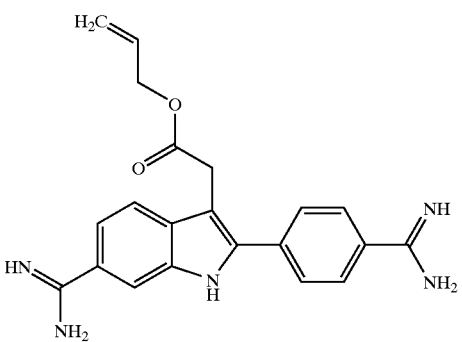

[6-Carbamimidoyl-2-(4-carbamimidoyl-phenyl)-1H-indol-3-yl]-acetic acid allyl ester dihydrochloride (2.0.26)

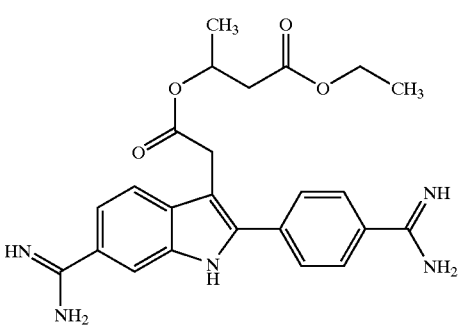

3-{[6-Carbamimidoyl-2-(4-carbamimidoyl-phenyl)-1H-indol-3-yl]-acetoxy}-butyric acid ethyl ester dihydrochloride (2.0.27)

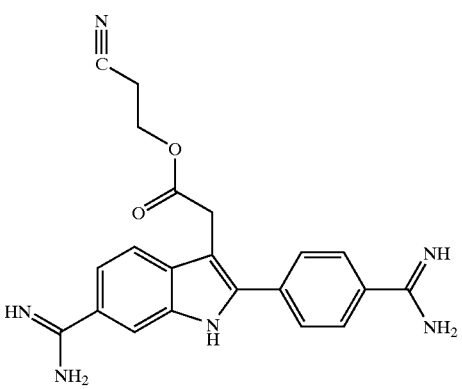

[6-Carbamimidoyl-2-(4-carbamimidoyl-phenyl)-1H-indol-3-yl]-acetic acid 2-cyano-ethyl ester dihydrochloride (2.0.28)

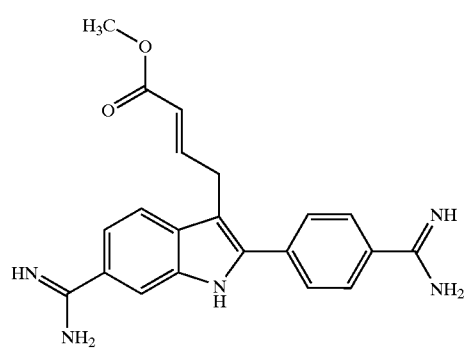

4-[6-Carbamimidoyl-2-(4-carbamimidoyl-
phenyl)-1H-indol-3-yl]-but-2-enoic acid
methyl ester dihydrochloride (2.0.29)

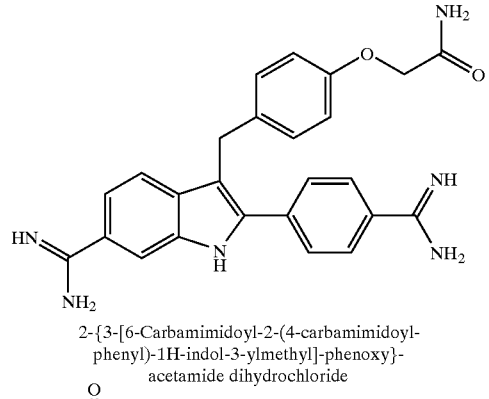

2-{3-[6-Carbamimidoyl-2-(4-carbamimidoyl-
phenyl)-1H-indol-3-ylmethyl]-phenoxy}-
acetamide dihydrochloride (2.0.30)

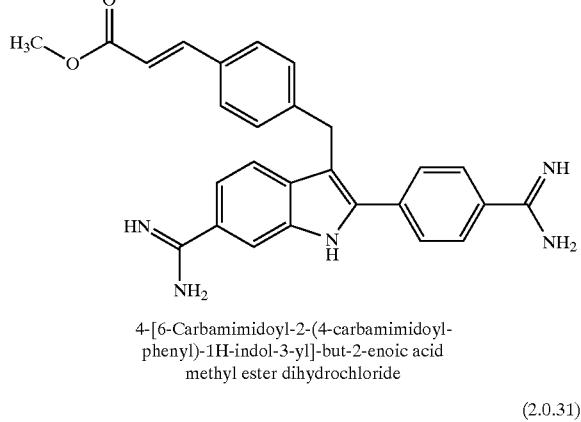

4-[6-Carbamimidoyl-2-(4-carbamimidoyl-
phenyl)-1H-indol-3-yl]-but-2-enoic acid
methyl ester dihydrochloride (2.0.31)

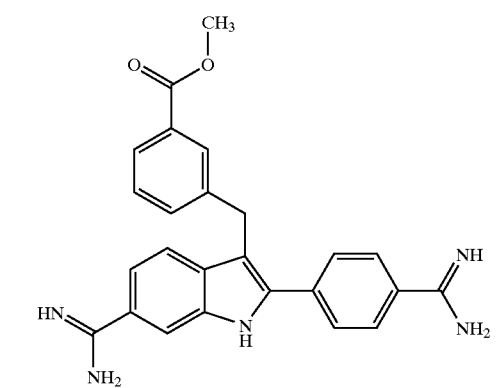

3-[6-Carbamimidoyl-2-(4-carbamimidoyl-
phenyl)-1H-indol-3-ylmethyl]-benzoic acid
methyl ester dihydrochloride (2.0.32)

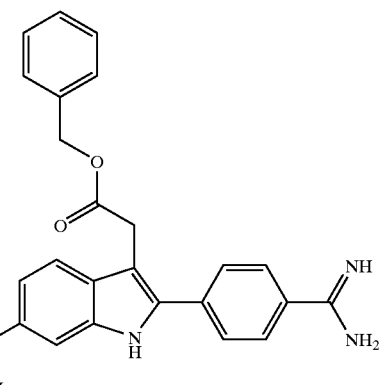

[6-Carbamimidoyl-2-(4-carbamimidoyl-
phenyl)-1H-indol-3-yl]acetic acid benzyl
ester dihydrochloride (2.0.33)

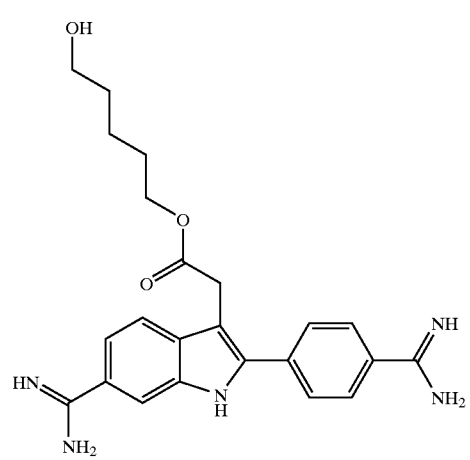

[6-Carbamimidoyl-2-(4-carbamimidoyl-
phenyl)-1H-indol-3-yl]acetic acid 5-hydroxy-
pentyl ester dihydrochloride (2.0.34)

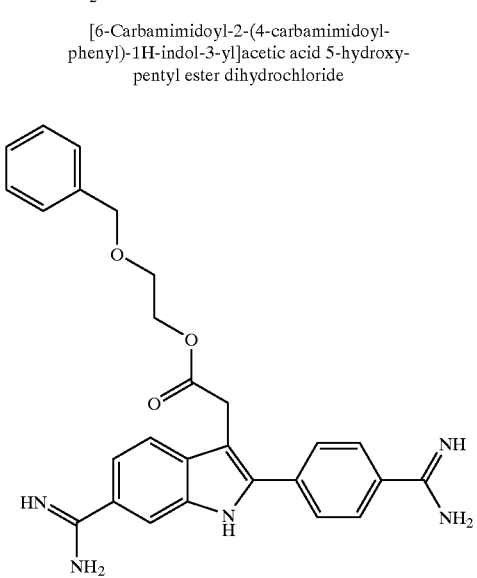

[6-Carbamimidoyl-2-(4-carbamimidoyl-
phenyl)-1H-indol-3-yl]acetic acid 2-
benzyloxy-ethyl ester dihydrochloride

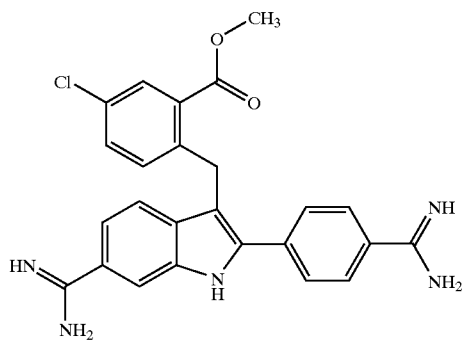

2-[6-Carbamimidoyl-2-(4-carbamimidoyl-phenyl)-1H-indol-3-ylmethyl]-5-chloro-benzoic acid methyl ester dihydrochloride (2.0.35)

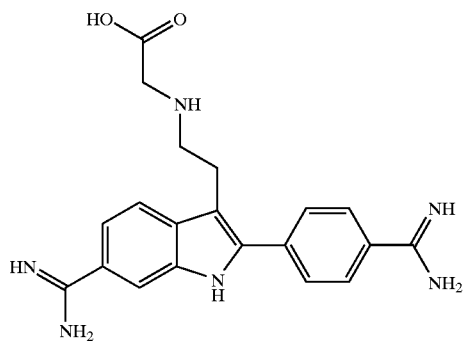

{2-[6-Carbamimidoyl-2-(4-carbamimidoyl-phenyl)-1H-indol-3-yl]-ethylamino}-acetic acid dihydrochloride (2.0.38)

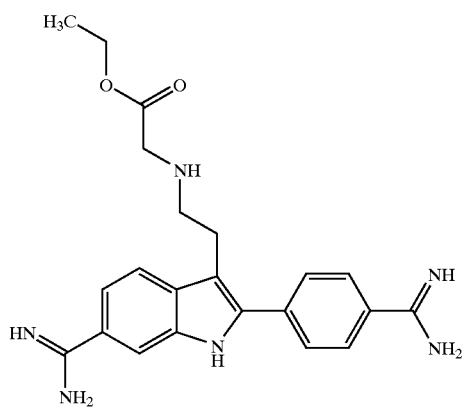

{2-[6-Carbamimidoyl-2-(4-carbamimidoyl-phenyl)-1H-indol-3-yl]-ethylamino}-acetic acid ethyl ester dihydrochloride (2.0.36)

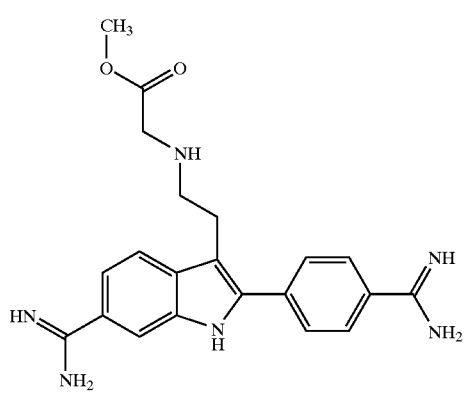

{2-[6-Carbamimidoyl-2-(4-carbamimidoyl-phenyl)-1H-indol-3-yl]-ethylamino}-acetic acid methyl dihydrochloride (2.0.39)

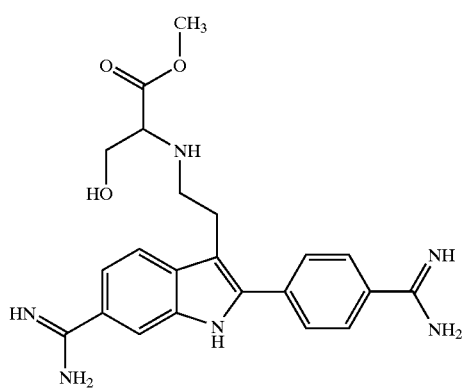

2-{2-[6-Carbamimidoyl-2-(4-carbamimidoyl-phenyl)-1H-indol-3-yl]-ethylamino}-3-hydroxy-propionic acid methyl ester dihydrochloride (2.0.37)

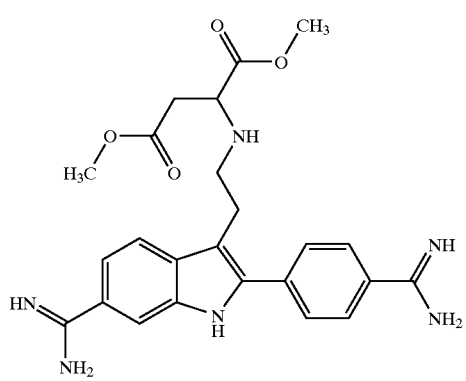

2-{2-[6-Carbamimidoyl-2-(4-carbamimidoyl-phenyl)-1H-indol-3-yl]-ethylamino}-succinic acid dimethl esterdihydrochloride (2.0.40)

(2.0.41)

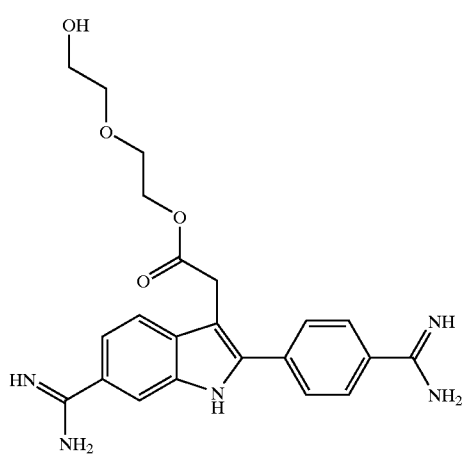

[6-Carbamimidoyl-2-(4-carbamimidoyl-phenyl)-1H-indol-3-yl]-acetic acid 2-(2-hydroxy-ethoxy)-ethyl ester dihydrochloride (2.0.44)

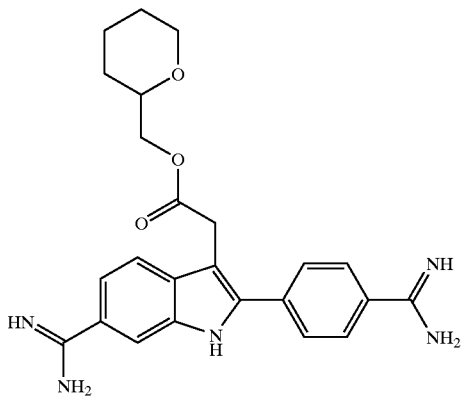

[6-Carbamimidoyl-2-(4-carbamimidoyl-phenyl)-1H-indol-3-yl]-acetic acid tetrahydro-pyran-2-ylmethyl ester dihydrochloride (2.0.42)

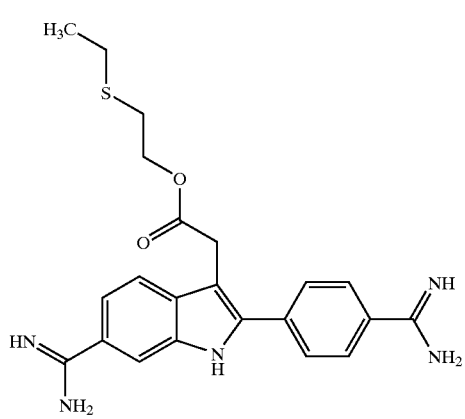

[6-Carbamimidoyl-2-(4-carbamimidoyl-phenyl)-1H-indol-3-yl]-acetic acid 2-ethylsulfanyl-ethyl ester dihydrochloride (2.0.45)

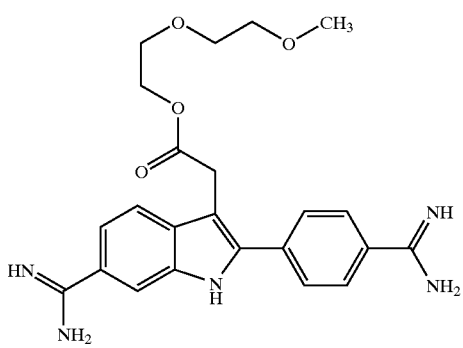

[6-Carbamimidoyl-2-(4-carbamimidoyl-phenyl)-1H-indol-3-yl]-acetic acid 2-(2-methoxy-ethoxy)-ethyl ester dihydrochloride (2.0.43)

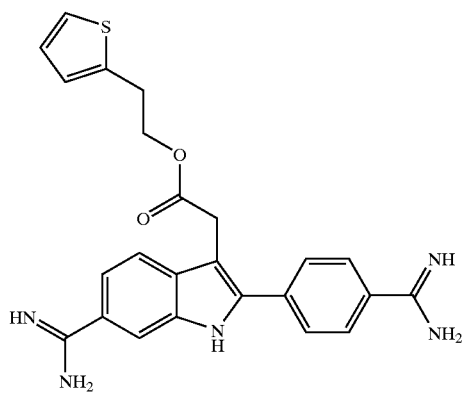

[6-Carbamimidoyl-2-(4-carbamimidoyl-phenyl)-1H-indol-3-yl]-acetic acid 2-thiophen-2-yl-ethyl ester dihydrochloride (2.0.46)

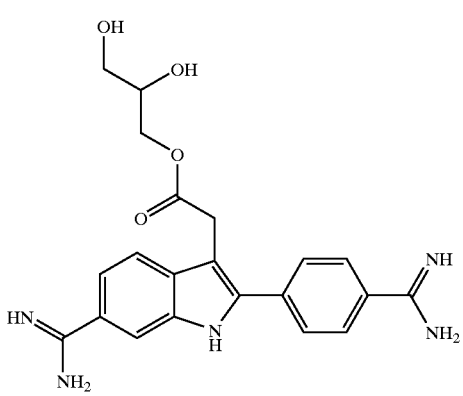

[6-Carbamimidoyl-2-(4-carbamimidoyl-phenyl)-1H-indol-3-yl]-acetic acid 2,3-dihydroxy-propyl ester dihydrochloride

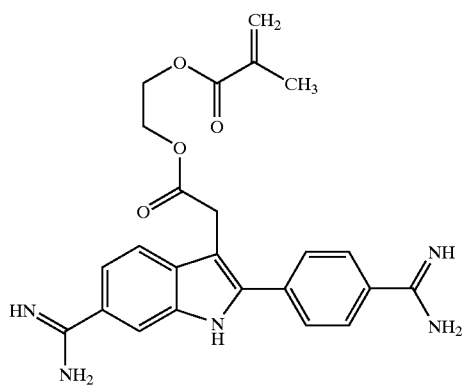

2-Methyl-acrylic acid 2-{[6-carbamimidoyl-2-
(4-carbamimidoyl-phenyl)-1H-indol-3-yl]-
acetoxy}-ethyl ester dihydrochloride (2.0.47)

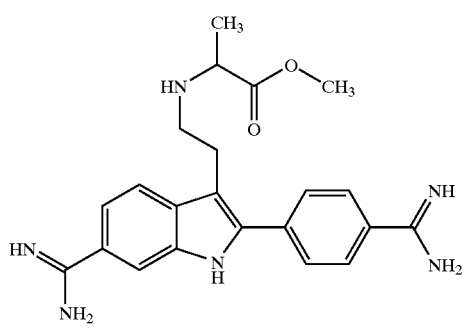

2-{2-[6-Carbamimidoyl-2-(4-carbamimidoyl-
phenyl)-1H-indol-3-yl]-ethylamino}-propionic
acid methyl ester dihydrochloride (2.0.48)

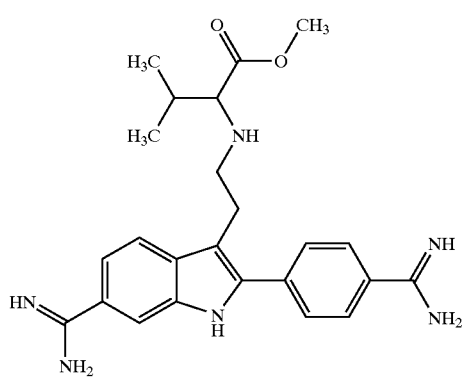

2-{2-[6-Carbamimidoyl-2-(4-carbamimidoyl-
phenyl)-1H-indol-3-yl]-ethylamino}-3-methyl-
butyric acid methyl ester dihydrochloride (2.0.49)

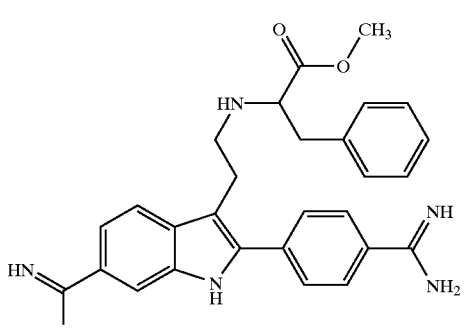

2-{2-[6-Carbamimidoyl-2-(4-carbamimidoyl-
phenyl)-1H-indol-3-yl]-ethylamino}-3-phenyl-
propionic acid methyl ester dihydrochloride (2.0.50)

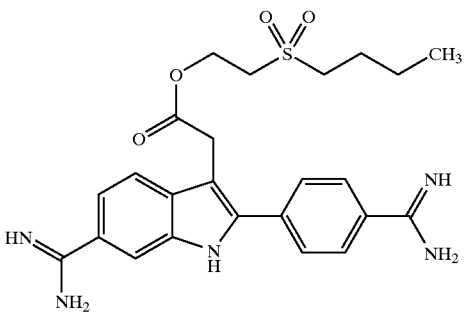

[6-Carbamimidoyl-2-(4-carbamimidoyl-
phenyl)-1H-indol-3-yl]-acetic acid 2-(butane-
1-sulfonyl)-ethyl ester dihydrochloride (2.0.51)

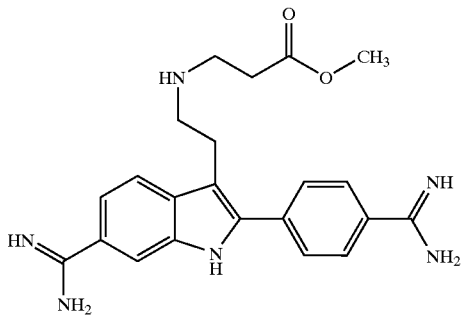

3-{2-[6-Carbamimidoyl-2-(4-carbamimidoyl-
phenyl)-1H-indol-3-yl]-ethylamino}-propionic
acid methyl ester dihydrochloride (2.0.52)

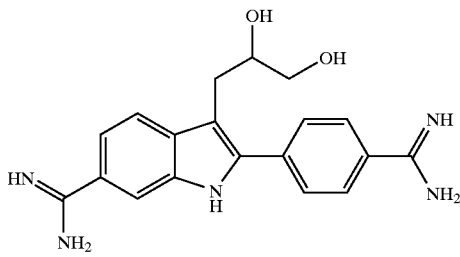

2-(4-Carbamimidoyl-phenyl)-3-(2,3-
dihydroxy-propyl)-1H-indole-6-carboxamidine
dihydrochloride (2.0.53)

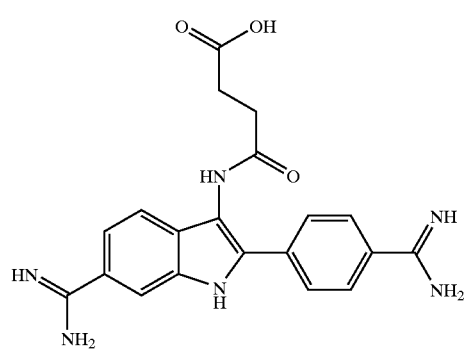

N-[6-Carbamimidoyl-2-(4-carbamimidoyl-
phenyl)-1H-indol-3-yl]-succunamic acid
dihydrochloride (2.0.54)

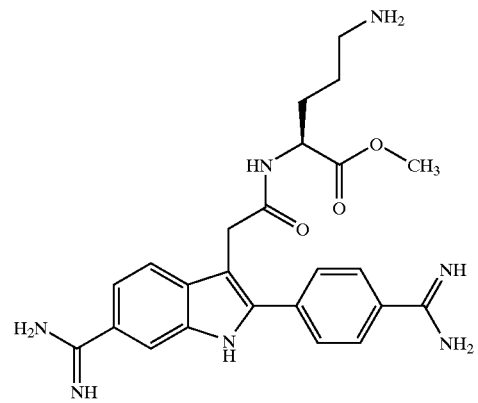

5-Amino-2-{2-[6-carbamimidoyl-2-(4-
carbamimidoyl-phenyl)-1H-indol-3-yl]-
acetylamino}-pentanoic acid methyl ester
dihydrochloride (2.0.57)

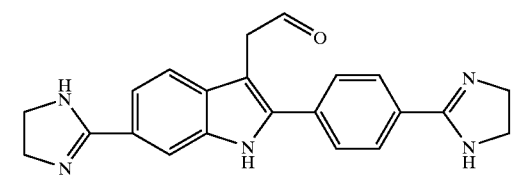

{6-(4,5-Dihydro-1H-imidazol-2-yl)-2-[4-(4,5-
dihydro-1H-imidazol-2-yl)-phenyl]-1H-indol-3-
yl}-acetaldehyde dihydrochloride (2.0.55)

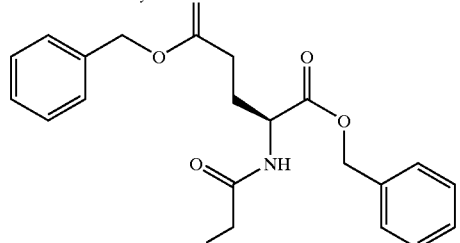

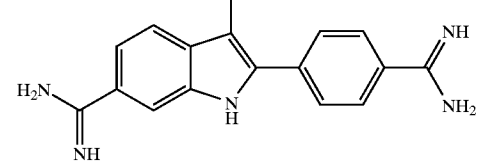

2-(2-{2-[6-Carbamimidoyl-2-(4-
carbamimidoyl-phenyl)-1H-indol-3-yl]-
acetylamino}-acetylamino)-pentanedioic acid
dibenzyl ester dihydrochloride (2.0.58)

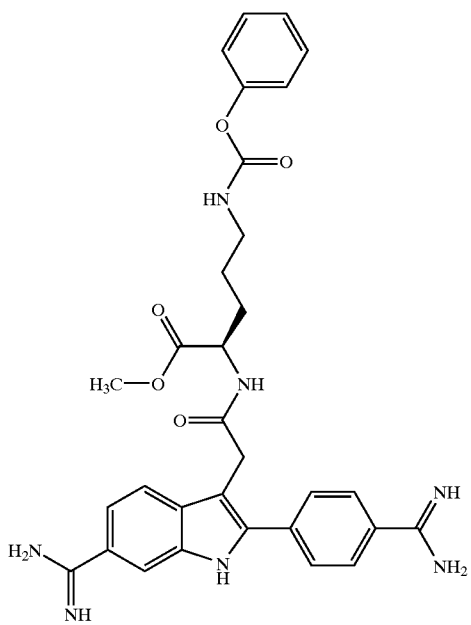

5-Benzyloxycarbonylamino-2-{2-[6-
carbamimidoyl-2-(4-carbamimidoyl-phenyl)-
1H-indol-3-yl]-acetylamino}-pentanoic acid
methyl ester dihydrochloride (2.0.56)

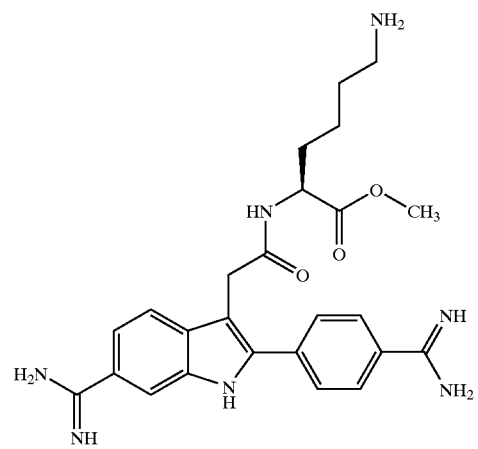

6-Amino-2-{2-[6-Carbamimidoyl-2-(4-
carbamimidoyl-phenyl)-1H-indol-3-yl]-
acetylamino}haxanoic acid methyl ester
dihydrochloride (2.0.59)

The above-described compounds of Formula (1.0.0) may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures well known in the art. Such well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such agents as ($C_1$–$C_4$) alkyl halides, e.g., methyl, ethyl, iso-propyl and tert-butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and stearyl chlorides, bromides and iodides; and aryl-($C_1$–$C_4$) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described antiproliferative compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipient, adjuvants and vehicles. Pharmaceutically acceptable carriers that may be used in the pharmaceutical compositions of this invention include but are not limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the diluents, excipient, adjuvants and vehicles used in the pharmaceutical compositions of the present invention comprise members selected from the groups consisting essentially of the following: acidifying and alkalizing agents added to obtain a desired or predetermined pH comprise acidifying agents, e.g., acetic acid, glacial acetic acid, malic acid, and propionic acid, and alkalizing agents, e.g., edetol, potassium carbonate, potassium hydroxide, sodium borate, sodium carbonate, and sodium hydroxide; aerosol propellants required where the pharmaceutical composition is to be delivered as an aerosol under significant pressure, e.g., acceptable halogenated hydrocarbons; nitrogen; or a volatile hydrocarbon such as butane, propane, isobutane or mixtures thereof; antimicrobial agents including antibacterial, antifungal and antiprotozoal agents added where the pharmaceutical composition is topically applied, e.g., antimicrobial agents such as benzyl alcohol, chlorobutanol, phenylethyl alcohol, phenylmercuric acetate, potassium sorbate, and sorbic acid, and antifungal agents such as benzoic acid, butylparaben, ethylparaben, methylparaben, propylparaben, and sodium benzoate; antimicrobial preservatives added to the pharmaceutical compositions in order to protect them against the growth of potentially harmful microorganisms, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol; antioxidants added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols; buffering agents used to maintain a desired pH of a composition once established, e.g., calcium acetate, potassium metaphosphate, potassium phosphate monobasic, and tartaric acid; and chelating agents used to help maintain the ionic strength of the pharmaceutical composition and bind to and effectively remove destructive compounds and metals, e.g., edetate dipotassium, edetate disodium, and edetic acid.

Dermatologically active agents are added to the pharmaceutical compositions of the present invention to be applied topically, e.g., wound healing agents such as peptide derivatives, yeast, panthenol, hexylresorcinol, phenol, tetracycline hydrochloride, lamin and kinetin, glucocorticosteroids for treating inflammation, e.g., hydrocortisone, dexamethasone, betamethasone, triamcinolone, fluocinolone and methylprednisolone, retinoids for treating acne, psoriasis, cutaneous aging, and skin cancer, e.g., retinol, tretinoin, isotretinoin, etretinate, acitretin, and arotinoid, immunosuppressive agents for treating inflammation, e.g., dapsone and sulfasalazine; mild antibacterial agents, e.g., resorcinol, salicylic acid, benzoyl peroxide, erythromycin-benzoyl peroxide, erythromycin, clindamycin, and mupirocin, antifungal agents, e.g., griseofulvin, azoles such as miconazole, econazole, itraconazole, fluconazole, and ketoconazole, and allylamines such as naftifine and terfinafine, antiviral agents, e.g., acyclovir, famciclovir, and valacyclovir, antihistamines, e.g., diphenhydramine, terfenadine, astemizole, loratadine, cetirizine, acrivastine, and temelastine, topical anesthetics, e.g., benzocaine, lidocaine, dibucaine, and pramoxine hydrochloride, topical analgesics, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Further examples of diluents, excipient, adjuvants and vehicles used in the pharmaceutical compositions of the present invention comprise members selected from the groups consisting essentially of the following: dispersing and suspending agents, e.g., poligeenan, povidone, and silicon dioxide; emollients, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., α-dodecyl-Ω-hydroxy-poly(oxy-1,2-ethanediyl) or polyethylene glycol monododecyl ether.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HCIX or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate , cetyl esters wax, cetearyl alcohol, 2-octyldodecanol, benzyl alcohol and water.

For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of a compound of Formula (1.0.0) effective for preventing, inhibiting, suppressing or reducing the unregulated differentiation of cells and cellular processes, and consequent or associated pathogenic processes mediated by the DNA methyl transferase enzyme will depend on a variety of factors, such as the chemical nature and biological activity of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of Formula (1.0.0) will be between about 1.0 $\mu$g and about 10.0 mg/kg body weight per day, preferably between about 5.0 $\mu$g and about 5.0 mg/kg body weight per day, more preferably between about 10.0 $\mu$g and about 1.0 mg/kg of body weight per day, and most preferably between about 20.0 $\mu$g and about 0.5 mg/kg of body weight per day of the active ingredient.

Where the dosage form is topically administered by means of an ointment, suitable dosage levels of a compound of Formula (1.0.0) will be between about 0.1 $\mu$g and about 1.0 mg/kg body weight per day, preferably between about 0.5 $\mu$g and about 0.5 mg/kg body weight per day, more preferably between about 1.0 $\mu$g and about 0.1 mg/kg of body weight per day, and most preferably between about 2.0 $\mu$g and about 0.05 mg/kg of body weight per day of the active ingredient.

Using representative body weights of 10 kg and 100 kg in order to illustrate the range of daily topical dosages which might be used as described above, suitable dosage levels of the compounds of Formula (1.0.0) will be between about 1.0–10.0 $\mu$g and 10.0–100.0 mg per day, preferably between about 5.0–50.0 $\mu$g and 5.0–50.0 mg per day, more preferably between about 10.0–100.0 $\mu$g and 1.0–10.0 mg per day, and most perferably between about 20.0–200.0 $\mu$g and about 0.5–5.0 mg per day of the active ingredient comprising a compound of Formula (1.0.0). These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy Numerous other factors must also be considered in deciding upon the number of doses per day and the amount of active ingredient per dose which will be administered. Not the least important of such other factors is the individual response of the patient being treated. Thus, for example, where the active ingredient is used to treat or prevent psoriasis, and is administered topically via ointment with from one to four applications, will be administered each day, each dose, i.e., ointment application containing from about 50.0 $\mu$g to about 10.0 mg of active ingredient.

Included within the scope of the present invention are embodiments comprising compositions which contain, in addition to a compound of the present invention as active ingredient, additional therapeutic agent active ingredients selected from the group consisting essentially of anti-inflammatory corticosteroids; non-steroidal anti-inflammatories; immunosuppressants; immunostimulants; antimetabolites; antipsoriatics, anti-cancer agents, and antidiabetics. Specific compounds within each of these classes may be selected from those listed under the appropriate headings in *Comprehensive Medicinal Chemistry*, Pergamon Press, Oxford, England, pp. 970–986 (1990); and *Goodman and Gilman's The Pharmacological Basis of Therapeutics*, 9th ed., Hardman, J. G. and Limbird, L. E., eds., McGraw-Hill, 1996, the disclosure of which are incorporated herein by reference in their entireties. Especially preferred active ingredients to be included for use in combination with the compounds of Formula (1.0.0) are anti-inflammatory compounds such as theophylline, sulfasalazine and aminosalicylates; immunosuppressants such as cyclosporin, FK-506, and rapamycin; antimetabolites such as cyclophosphamide and methotrexate; and immunomodulators such as the interferons.

Still further embodiments of the present invention relate to a method of treating a neoplastic or a non-neoplastic disease characterized by abnormally rapid proliferation of tissue involved in said disease, comprising administering to a patient in need of such treatment a therapeutically effective amount of a compound of Formula (1.0.0) as above described. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, pneumocyctis caring infection, and restenosis.

The present invention still further relates to a pharmaceutical composition for use as a DNA methyltransferase inhibiting agent, comprising a therapeutically effective amount of a heterocyclic bisamidine compound of Formula (1.0.0) as above described, together with a pharmaceutically acceptable carrier for said compound. The present invention relates as well to a corresponding method of treating a neoplastic or a non-neoplastic disease characterized by abnormally rapid proliferation of tissue involved in said disease which is mediated by or associated with abnormally increased levels of DNA methylation, comprising administering to a patient in need of such treatment a therapeutically effective amount of a compound of Formula (1.0.0) as above described. Said patient is a mammal, including especially a human. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *pneumocyctis carinii* infection, and restenosis.

Antineoplastic and antiproliferative agents of the present invention may also be used in the therapy of psoriasis, a non-neoplastic disease of the skin characterized by abnormally rapid proliferation of epidermal cells, as well as for the beneficial treatment of *Pneumocystis carinii*. Therapeutic agents of the present invention are useful in the treatment of proliferative diseases such as restenosis, in addition to cancer and psoriasis.

The above-described methods of treatment of the present invention may employ the compounds of Formula (1.0.0) in the form of monotherapy, but said methods may also be used in the form of multiple therapy in which one or more compounds of Formula (1.0.0) are co-administered in combination with a known anti-inflammatory, immunomodulating, immunostimulating or immunosuppressive agent. The terms "co-administered" or "co-administration" as used herein are intended to mean therapeutic utilization of one or more compounds of Formula (1.0.0) in combination with one or more additional therapeutic agents, including but not limited to, administration of the combination of therapeutic active agents in a single dosage form or in multiple dosage forms representing the same or different routes of administration, said multiple dosage forms being administered at substantially the same time or at different times.

Subsequent to synthesis of any of the above-recited preferred species of the present invention or any other compounds falling within the scope of Formula (1.0.0), the biological activities relating to the DNA methyltransferase inhibitory specificities of said compounds may be determined using one or more of the numerous in vitro and in vivo assays which have been described heretofore in the technical literature pertinent to the art. For example, some of the now very-well established assay methods and models concern measurement of DNA methyltransferase inhibitory activity by determining the concentration of a test candidate inhibitor required to block the binding of DNA methyltransferase contained in a cell lysate to a substrate for said enzyme consisting of poly(dl-dC):(dl-dC). The methyl donor S-adenosyl-L-[methyl $^3$H] methionine (SAM) is also present. After incubation the methylated poly(dl-dC):(dl-dC) product is collected on a filter such as DEAE-Sephadex, epichlorohydrin crosslinked dextran 2-(diethylamino)ethyl 2-[[2-(diethylamino)ethyl]diethylammonio]ethyl ether chloride hydrochloride, and after drying, the amount of said product bound to said filter is determined by scintillation counting.

The compounds of the present invention may be formulated into pharmaceutical compositions that may be administered orally, parenterally, by inhalation (metered dose inhaler, dry powder inhaler or nebulizer), topically, rectally, nasally, intraocularly, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The compounds of Formula (1.0.0) may be prepared in accordance with well-known procedures for carrying out the synthesis of organic compounds. A number of different procedures are available which are fully disclosed in the technical literature and with which the skilled artisan will be familiar. The description which follows of such a synthesis scheme is merely representative and not intended to be in any way a limitation of the scope of the present invention.

In Step a of Synthesis Scheme 1, a 4-formyl benzonitrile having the desired $R^{15}$ substituent (3.0.1) is reacted with a 4-methyl-3-nitro benzonitrile having the desired $R^{17}$ substituent (3.0.2), in the presence of a base such as sodium methoxide, in a polar, aprotic solvent such as dimethylsulfoxide (DMSO). The reaction mixture is maintained below room temperature. The adduct which is formed is an alcohol (3.0.3).

In Step b of Synthesis Scheme 1, (3.0.3), which is a secondary alcohol, is treated with Jones reagent, an aqueous solution of chromic acid and sulfuric acid, in a polar, solvent such as acetone. The reaction mixture is maintained below room temperature, and the Jones reagent quickly oxidizes the alcohol (3.0.3) to the corresponding ketone (3.0.4).

In Step c of Synthesis Scheme 1, the desired substituent $R^{14}$ is attached to ketone (3.0.4), which already includes the desired substituents $R^{15}$ and $R^{17}$, by treatment with a bromine reagent which includes the $R^{14}$ moiety. For example, where it is desired to attach an allyl group as defining $R^{14}$, the reagent used is allyl bromide. Potassium carbonate, $K_2CO_3$, is added to the reaction mixture using a polar, aprotic solvent such as dry acetone, after which the reaction mixture is heated at reflux for from 1 to 3 hours, preferably 2 hours. The product containing the desired $R^{14}$ substituent, (3.0.5), is isolated for use in the next step of the synthesis.

In Step d of Synthesis Scheme 1, the intermediate (3.0.5) is cyclized to form the indolyl-2-phenyl intermediate (3.0.6). This ring closure is carried out using zinc dust in the presence of acetic acid, with reflux of the reaction mixture.

In Step e of Synthesis Scheme 1, the two nitrile groups attached to the indolyl-2-phenyl intermediate (3.0.6) are converted to the corresponding imino ester (imidate) salts in accordance with the conditions required for carrying out the well-known Pinner Reaction. Intermediate (3.0.6) is dissolved in a dry HCl solution of 2-methoxyethanol to which anhydrous methanol is then added. There results the hydrochloride salt of each imino methyl ester, as shown in (3.0.7).

In Step f of Synthesis Scheme 1, the final product (3.0.8) is obtained as the dihydrochloride salt. Final product (3.0.8) contains the unsubstituted carbamimidoyl/carboxamidine moieties of the compounds of Formula (1.0.0).

Synthesis Scheme 1

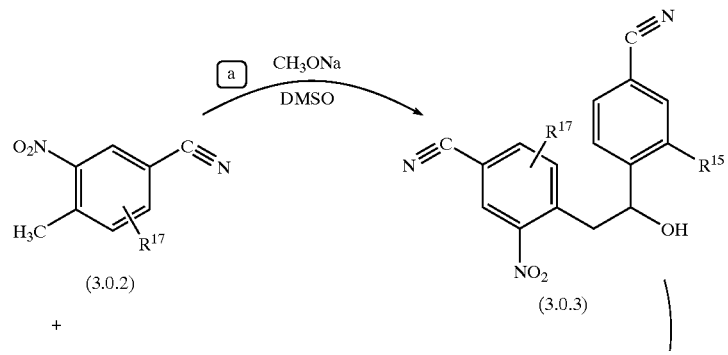

-continued

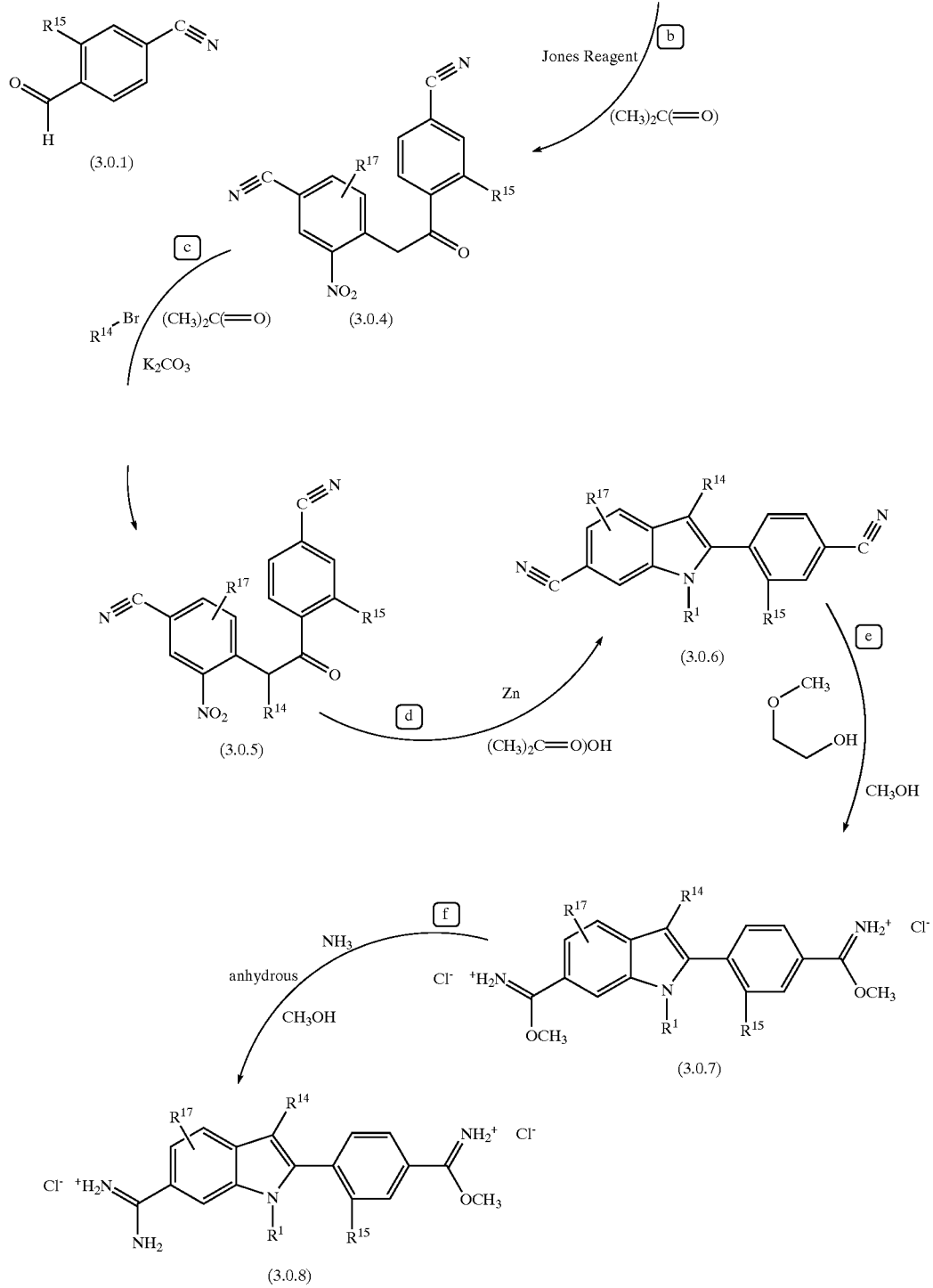

EXEMPLIFICATION OF PREFERRED EMBODIMENTS

There follows a description of preparation and working examples by means of which certain recited compounds of Formula (1.0.0) have been prepared, and by means of which other compounds falling within the scope of Formula (1.0.0) may be prepared in the future by a person having ordinary skill in this art. Said description is presented for the purpose of aiding the person of ordinary skill in making compounds of the present invention, although the instant specification when used in light of the knowledge and experience of such a person of ordinary skill, should prove to be completely adequate and free of ambiguity. Accordingly, the description which follows is not intended to in any way limit the scope of the present invention, and it should not be used in that way. The claims appended hereto define the intended scope of the present invention.

EXAMPLE 1

3-Allyl-2-(4-carbamimidoyl-phenyl)1H-indole-6-carboxamidine Dihydrochloride (3.1.8)

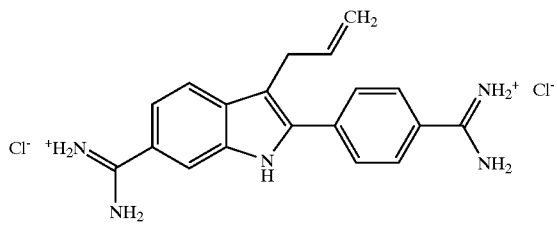

(3.1.8)

A. 2-(4-Cyano-2-nitro-phenyl)-1-(4-cyano-phenyl)-ethanol

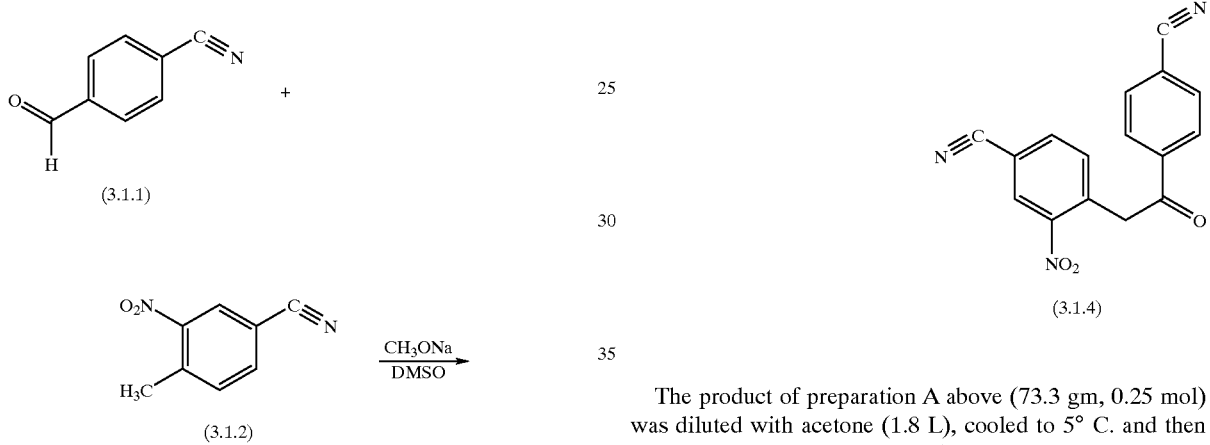

To a 10° C. solution of 4-formyl benzonitrile (65.6 gm, 0.500 mol), 4-methyl-3-nitro benzonitrile (81.1 gm, 0.500 mol) and 750 mL of dry dimethylsulfoxide (DMSO), was added sodium methylate (4.01 gm, 75 mmol) in one portion. After 4 hrs, the reaction was added dropwise to 6 L of ice water and then allowed to stir for 1 hr. The product was collected via vacuum filtration and washed with water (3×1 L) and then dried over night in a vacuum oven at 40° C. to give 2-(4-cyano-2-nitro-phenyl)-1-(4-cyano-phenyl)-ethanol.

B. 2-(4-Cyano-2-nitro-phenyl)-1-(4-cyano-phenyl)-ethanone

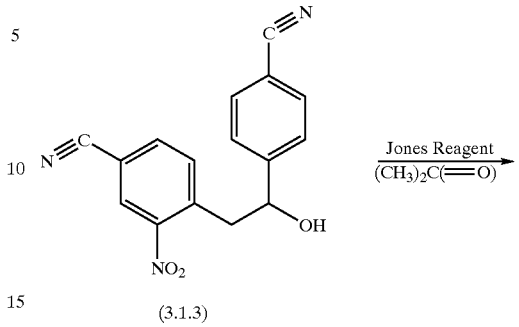

The product of preparation A above (73.3 gm, 0.25 mol) was diluted with acetone (1.8 L), cooled to 5° C. and then freshly prepared Jones reagent (53.4 gm $CrO_3$ dissolved in 46 mL conc. $H_2SO_4$ and diluted to 200 mL with $H_2O$) was added at such a rate that the temperature remained below 10° C. The reaction was filtered through. Celite brand of diatomaceous earth and the residue washed with acetone (600 mL). The combined filtrates were concentrated and then triturated with water (500 mL). The resultant yellow solid was collected via vacuum filtration and washed with water (900 mL) to afford 65.0 gm of 2-(4-cyano-2-nitro-phenyl)-1-(4-cyano-phenylethanone. A sample was recrystallized from acetonitrile to give a tan solid, mp 191–192° C.

C. 2-(4-Cyano-2-nitro-phenyl)-2-allyl-1-(4-cyano-phenyl)-ethanone

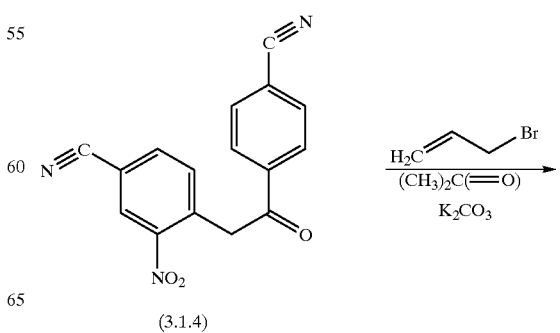

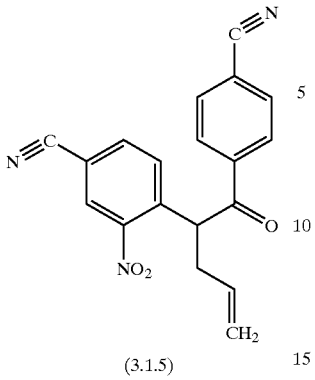

(3.1.5)

To a solution of the product of preparation B above (1.46 gm, 5.00 mmol) and dry acetone (25 mL) was added K$_2$CO$_3$ (0.87 gm, 6.3 mmol). The reaction turned deep violet, allyl bromide (0.69 mL, 8.0 mmol) was added in one portion and the reaction was then heated to reflux for 2 h. After cooling, the crude reaction mixture was concentrated to a small volume and poured into water (50 mL). The aqueous mixture was extracted with EtOAc (2×30 mL) and the combined organic layers were washed with 1N HCl (20 mL), water (2×20 mL) and brine (20 mL), dried over MgSO4 and concentrated to give 1.52 gm of 2-(4-cyano-2-nitro-phenyl)-2-allyl-1-(4-cyano-phenyl)-ethanone isolated as an oil.

D. 3-Allyl-2-(4-cyano-phenyl)-1H-indole-6-carbonitrile

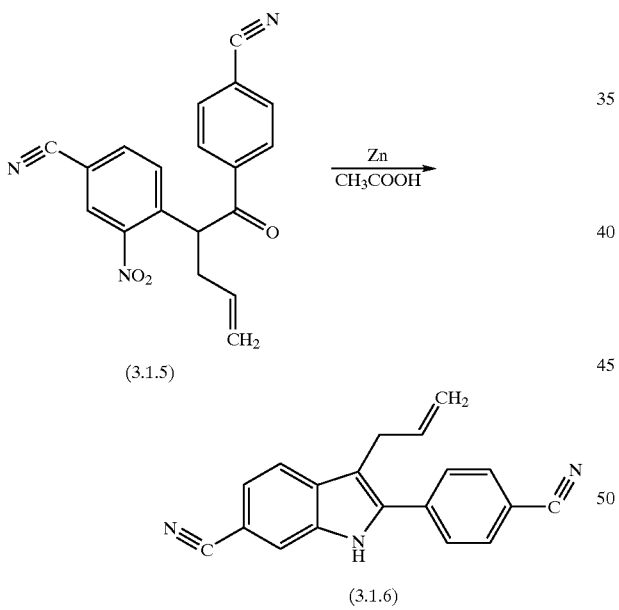

To a solution of all of the product of preparation C above (1.52 gm, 4.6 mmol) and acetic acid (30 mL) was added zinc dust (2.0 gm). The reaction was heated to reflux for 30 min, filtered while still hot and the residue washed with acetic acid (30 mL). The combined filtrates were cooled, the resultant crystals collected and washed with sequentially with ether (20 mL), 5% NaHCO$_3$ (50 mL), water (50 mL) and dried overnight at 60° C. under vacuum. 3-Allyl-2-(4-cyano-phenyl)-1H-indole-6-carbonitrile (1.18 gm) was isolated as a dark yellow solid, mp 217–221° C.

E. 3-Allyl-2-(4carbamimidoyl-phenyl)-1H-indole-6-carboxamidine bis Methyl Ester Dihydrochloride

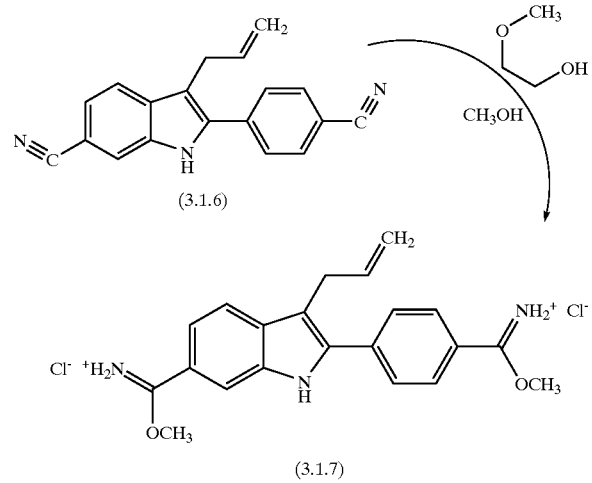

To a solution of the product of preparation D above (0.50 gm, 1.7 mmol) and an HCl saturated solution of 2-methoxyethanol (40 mL) was added anhydrous methanol (5 mL). The reaction was securely stoppered and stirred at ambient temperature for 25 h, diluted with ether (100 mL) and the resultant solid (0.71 gm) collected by vacuum filtration, 3-allyl-2-(4-carbamimidoyl-phenyl)-1H-indole-6-carboxamidine bis methyl ester dihydrochloride, mp 233–237° C.

F. 3-Allyl-2-(4-carbamimidoyl-phenyl)-1H-indole-6-carboxamidine Dihydrochioride

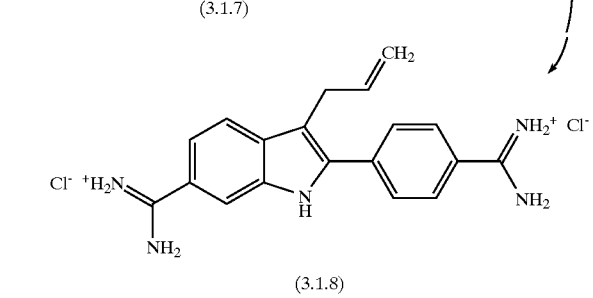

To a solution of methanol (40 mL) that had been saturated with anhydrous ammonia was added the bis-imidate ester salt (0.50 gm) prepared in preparation E above. After stirring for 72 h, the reaction was concentrated and the resulting solid was slurried in 3N HCl (20 mL), collected by vacuum filtration and washed with acetone (60 mL). After drying overnight at 80° C., 3-Allyl-2-(4-carbamimidoyl-phenyl)-1H-indole-6-carboxamidine dihydrochloride (428 mg) was isolated as a yellow solid, mp 328° C. (decomposition). $^1$H NMR (400 Mhz, d$_6$-DMSO) d12.3 (br s, 1H), 9.5 (br s, 1H), 9.3 (br s, 2H), 9.1 (br s, 1H), 7.99 (d, J=8.3 Hz, 2H), 7.94 (s, 1H), 7.86 (d, J=8.3 Hz, 2H), 7.71 (d, J=8.5, 1H), 7.43 (dd, J=1.5, 8.4 Hz, 1H), 6.04 (add, J=5.0, 10.1, 17.0 Hz, 1H), 5.01 (dd, J=1.6, 10.1 Hz, 1H), 4.92 (dd, J=1.6, 17.0 Hz, 1H), 3.64 (d, J=5.0 Hz, 1H), $^{13}$C NMR (100 Mhz, d$_6$-DMSO) d 27.8, 111.0, 111.9, 114.9, 117.9, 118.8, 120.6, 126.5, 127.4, 128.2, 132.0, 134.8, 136.2, 136.4, 136.5, 164.8, 166.1.

EXAMPLES 2–60

Following the procedures described above, but replacing key reactants with those which will provide the desired final product, the following specific embodiments of the compounds of Formula (1.0.0) are prepared:

| Example | Heterocyclic Bis Amidine Prepared | Melting point (° C.) |
|---|---|---|
| 2 | N-Methyl-2-[4-(N-methylcarbamimidoyl)-phenyl]-1H-indole-6-carboxamidine dihydrochloride | 282 |
| 3 | 6-(4,5-Dihydro-1H-imidazol-2-yl)-2-[4-(4,5-dihydro-1H-imidazol-2-yl)-phenyl]-5-fluoro-1H-indole dihydrochloride | >250 |
| 4 | 2-(4-Carbamimidoyl-2-hydroxy-phenyl)-1H-indole-6-carboxamidine dihydrochloride | >300 |
| 5 | [6-Carbamimidoyl-2-(4-carbamimidoyl-phenyl)-1H-indol-3-yl]-acetic acid dihydrochloride | >250 |
| 6 | 2-[4-Carbamimidoyl-2-(2-hydroxy-ethoxy)-phenyl]-1H-indole-6-carboxamidine dihydrochloride | |
| 7 | 2-(4-Carbamimidoyl-2-methoxy-phenyl)-1H-indole-6-carboxamidine dihydrochloride | >250 |
| 8 | [6-Carbamimidoyl-2-(4-carbamimidoyl-phenyl)-1H-indol-3-yl]-acetic acid isopropyl ester dihydrochloride | |
| 9 | [6-Carbamimidoyl-2-(4-carbamimidoyl-phenyl)-1H-indol-3-yl]-acetic acid sec-butyl ester dihydrochloride | |
| 10 | 2-[5-Carbamimidoyl-2-(6-carbamimidoyl-1H-indol-2-yl)-phenoxy]-propionic acid isopropyl ester dihydrochloride | 240 |
| 11 | 2-[4-Carbamimidoyl-2-(2,3-dihydroxy-propoxy)-phenyl]-1H-indole-6-carboxamidine dihydrochloride | >320 |
| 12 | [6-Carbamimidoyl-2-(4-carbamimidoyl-phenyl)-1H-indol-3-yl]-acetic acid butyl ester dihydrochloride | >270 |
| 13 | [6-Carbamimidoyl-2-(4-carbamimidoyl-phenyl)-1H-indol-3-yl]-acetic acid propyl ester dihydrochloride | >270 |
| 14 | 2-[6-Carbamimidoyl-2-(4-carbamimidoyl-phenyl)-1H-indol-3-yl]-propionic acid dihydrochloride | >260 |
| 15 | {6-(4,5-Dihydro-1H-imidazol-2-yl)-2-[4-(4,5-dihydro-1H-imidazol-2-yl)-phenyl]-1H-indol-3-yl}-acetic acid dihydrochloride | >300 |
| 16 | {6-(4,5-Dihydro-1H-imidazol-2-yl)-2-[4-(4,5-dihydro-1H-imidazol-2-yl)-phenyl]-1H-indol-3-yl}-acetic acid ethyl ester dihydrochloride | >300 |
| 17 | {6-Carbamimidoyl-2-[4-(4,5-dihydro-1H-imidazol-2-yl)-phenyl]-1H-indol-3-yl}-acetic acid dihydrochloride | |
| 18 | [6-Carbamimidoyl-2-(4-carbamimidoyl-2-methoxy-phenyl)-1H-indol-3-yl]-acetic acid ethyl ester dihydrochloride | |
| 19 | 4-[6-Carbamimidoyl-2-(4-carbamimidoyl-phenyl)-1H-indol-3-ylmethyl]-benzoic acid methyl ester dihydrochloride | >250 |
| 20 | 2-[6-Carbamimdoyl-2-4(4-carbamimidoyl-phenyl)-1H-indol-3-yl]-propionic acid methyl ester dihydrochloride | >250 |
| 21 | 5-[6-Carbamimidoyl-2-(4-carbamimidoyl-phenyl)-1H-indol-3-ylmethyl-]furan-2-carboxylic acid methyl ester dihydrochloride | >250 |
| 22 | [6-Carbamimidoyl-2-(4-carbamimidoyl-phenyl)-1H-indol-3-yl]-acetic acid 2-methoxy-ethyl ester dihydrochloride | >250 |
| 23 | [6-Carbamimidoyl-2-(4-carbamimidoyl-phenyl)-1H-indol-3-yl]-acetic acid 2-hydroxy-ethyl ester dihydrochloride | >250 |
| 24 | 2-[6-Carbamimidoyl-2-(4-carbamimidoyl-phenyl)-1H-indol-3-ylmethy]-benzoic acid methyl ester dihydrochloride | >250 |
| 25 | [6-Carbamimidoyl-2-(4-carbamimidoyl-2-hydroxy-phenyl)-1H-indol-3-yl]-acetic acid methyl ester dihydrochloride | >250 |
| 26 | [6-Carbamimidoyl-2-(4-carbamimidoyl-phenyl)-1H-indol-3-yl)-acetic acid allyl ester dihydrochloride | >250 |
| 27 | 3-{[6-Carbamimidoyl-2-(4-carbamimidoyl-phenyl)-1H-indol-3-yl]- acetoxy}-butyric acid ethyl ester dihydrochloride | >250 |

-continued

| Example | Heterocyclic Bis Amidine Prepared | Melting point (° C.) |
|---|---|---|
| 28 | [6-Carbamimidoyl-2-(4-carbamimidoyl-phenyl)-1H-indol-3-yl]-acetic acid 2-cyano-ethyl ester dihydrochloride | >250 |
| 29 | 4-[6-Carbamimidoyl-2-(4-carbamimidoyl-phenyl)-1H-indol-3-yl]-but-2-enoic acid methyl ester dihydrochloride | >250 |
| 30 | 2-{3-[6-Carbamimidoyl-2-(4-carbamimidoyl-phenyl)-1H-indol-3-ylmethyl]-phenoxy}-acetamide dihydrochloride | >250 |
| 31 | 3-{4-[6-Carbamimidoyl-2-(4-carbamimidoyl-phenyl)-1H-indol-3-ylmethyl]-phenyl}-acrylic acid methyl ester dihydrochloride | >250 |
| 32 | 3-[6-Carbamimidoyl-2-(4-carbamimidoyl-phenyl)-1H-indol-3-ylmethyl]-benzoic acid methyl ester dihydrochloride | >250 |
| 33 | [6-Carbamimidoyl-2-(4-carbamimidoyl-phenyl)-1H-indol-3-yl]-acetic acid benzyl ester dihydrochloride | >250 |
| 34 | [6-Carbamimidoyl-2-(4-carbamimidoyl-phenyl)-1H-indol-3-yl]-acetic acid 5-hydroxy-pentyl ester dihydrochloride | >250 |
| 35 | [6-Carbamimidoyl-2-(4-carbamimidoyl-phenyl)-1H-indol-3-yl]-acetic acid 2-benzyloxy-ethyl ester dihydrochloride | >250 |
| 36 | 2-[6-Carbamimidoyl-2-(4-carbamimidoyl-phenyl)-1H-indol-3-ylmethyl]-5-chloro-benzoic acid methyl ester dihydrochloride | >250 |
| 37 | {2-[6-Carbamimidoyl-2-(4-carbamimidoyl-phenyl)-1H-indol-3-yl]-ethylamino}-acetic acid dihydrochloride | >250 |
| 38 | {2-[6-Carbamimidoyl-2-(4-carbamimidoyl-phenyl)-1H-indol-3-yl]-ethylamino}-acetic acid methyl ester dihydrochloride | >250 |
| 39 | {2-[6-Carbamimidoyl-2-(4-carbamimidoyl-phenyl)-1H-indol-3-yl]-ethylamino}-acetic acid ethyl ester dihydrochloride | >250 |
| 40 | 2-{2-[6-Carbamimidoyl-2-(4-carbamimidoyl-phenyl)-1H-indol-3-yl]-ethylamino}-3-hydroxy-propionic acid methyl ester dihydrochloride | >250 |
| 41 | 2-{2-[6-Carbamimidoyl-2-(4-carbamimidoyl-phenyl)-1H-indol-3-yl]-ethylamino}-succinic acid dimethyl ester dihydrochloride | >250 |
| 42 | [6-Carbamimidoyl-2-(4-carbamimidoyl-phenyl)-1H-indol-3-yl]-acetic acid 2-(2-hydroxy-ethoxy)-ethyl ester dihydrochloride | >250 |
| 43 | [6-Carbamimidoyl-2-(4-carbamimidoyl-phenyl)-1H-indol-3-yl]-acetic acid 2-ethylsulfanyl-ethyl ester dihydrochloride | >250 |
| 44 | [6-Carbamimidoyl-2-(4-carbamimidoyl-phenyl)-1H-indol-3-yl]-acetic acid 2-thiophen-2-yl-ethyl ester dihydrochloride | >250 |
| 45 | [6-Carbamimidoyl-2-(4-carbamimidoyl-phenyl)-1H-indol-3-yl]-acetic acid tetrahydro-pyran-2-ylmethyl ester dihydrochloride | >250 |
| 46 | [6-Carbamimidoyl-2-(4-carbamimidoyl-phenyl)-1H-indol-3-yl]-acetic acid 2-(2-methoxy-ethoxy)-ethyl ester dihydrochloride | >250 |
| 47 | [6-Carbamimidoyl-2-(4-carbamimidoyl-phenyl)-1H-indol-3-yl]-acetic acid 2,3-dihydroxy-propyl ester dihydrochloride | >250 |
| 48 | 2-Methyl-acrylic acid 2-{[6-carbamimidoyl-2-(4-carbamimidoyl-phenyl)-1H-indol-3-yl])-acetoxy}-ethyl ester dihydrochloride | >250 |
| 49 | 2-{2-[6-Carbamimidoyl-2-(4-carbamimidoyl-phenyl)-1H-indol-3-yl]-ethylamino}-propionic acid methyl ester dihydrochloride | >250 |
| 50 | 2-{2-[6-Carbamimidoyl-2-(4-carbamimidoyl-phenyl)-1H-indol-3-yl]-ethylamino}-3-methyl-butyric acid methyl ester dihydrochloride | >250 |
| 51 | 2-{2-[6-Carbamimidoyl-2-(4-carbamimidoyl-phenyl)-1H-indol-3-yl]-ethylamino}-3-phenyl-propionic acid methyl ester dihydrochloride | >250 |
| 52 | [6-Carbamimidoyl-2-(4-carbamimidoyl-phenyl)-1H-indol-3-yl]-acetic acid 2-(butane-1-sulfonyl)-ethyl ester dihydrochloride | >250 |

-continued

| Example | Heterocyclic Bis Amidine Prepared | Melting point (° C.) |
|---|---|---|
| 53 | 3-{2-[6-Carbamimidoyl-2-(4-carbamimidoyl-phenyl)-1H-indol-3-yl]-ethylamino}-propionic acid methyl ester dihydrochloride | >250 |
| 54 | 2-(4-Carbamimidoyl-phenyl)-3-(2,3-dihydroxy-propyl)-1H-indole-6-carboxamidine dihydrochloride | >250 |
| 55 | {6-(4,5-Dihydro-1H-imidazol-2-yl)-2-[4-(4,5-dihydro-1H-imidazol-2-yl)-phenyl]-1H-indol-3-yl}-acetaldehyde dihydrochloride | >300 |
| 56 | N-[6-Carbamimidoyl-2-(4-carbamimidoyl-phenyl)-1H-indol-3-yl]-succinamic acid dihydrochloride | >250 |
| 57 | 5-Benzyloxycarbonylamino-2-{2-[6-carbamimidoyl-2-(4-carbamimidoyl-phenyl)-1H-indol-3-yl]-acetylamino}-pentanoic acid methyl ester dihydrochloride | 230–235 |
| 58 | 5-Amino-2-{2-[6-carbamimidoyl-2-(4-carbamimidoyl-phenyl)-1H-indol-3-yl]-acetylamino}-pentanoic acid methyl ester dihydrochloride | >250 |
| 59 | 2-(2-{2-[6-Carbamimidoyl-2-(4-carbamimidoyl-phenyl)-1H-indol-3-yl]-acetylamino}-acetylamino)-pentanedioic acid dibenzyl ester dihydrochloride | 207–212 |
| 60 | 6-Amino-2-{2-[6-carbamimidoyl-2-(4-carbamimidoyl-phenyl)-phenyl)-1H-indol-3-yl]-acetylamino}-hexanoic acid methyl ester dihydrochloride | >260 |

EXAMPLE 61

DNA Methyltransferase Inhibition Study

Materials: The DNA methyltransferase enzyme used in these studies was prepared from Friend murine erythroleukemia cells. The cofactor S-adenosyl-L-[methyl $^3$H]methionine (SAM) was purchased from Amersham Life Science Products. The substrate poly (dl-dC):(dl-dC) and other reagents were purchased from Sigma Chemicals.

Lysate Preparation: The method of cell lysate preparation utilized in this procedure was essentially the same as that described in Kumar, et aL., *Biochemistry*, 31(36): 8648–8653 (1992). The cells were grown in suspension, harvested by centrifugation and lysed by 2×30 second pulses of sonication in 5 pellet volumes of lysis buffer (20 mM TrisHCl, pH 7.4, 400 mM NaCl, 5 mM EDTA, 0.1% Nonidet P-40, 25% glycerol, 1 mM Phenylmethylsulfonyl fluoride (PMSF)). The lysed cells were then extracted with an equal volume of pre-equilibrated DEAE-Sepharose and allowed to incubate on ice for 10 minutes, after which the supernatant was recovered by centrifugation at 6000×g. The supernatant was again cleared at 12,000×g and the lysate was aliquoted and stored at −80° C.

Methyltransferase Reaction: The DNA methyltransferase assay was run in assay buffer containing: 20 nM TrisHCl, pH 7.4, 1 nM EDTA, 10% glycerol, 1 mM DTT, 1 mM PMSF. The cell lysate containing the methyltransferase enzyme was added to a concentration of 5 µg protein per reaction. The substrate poly (dl-dC):(dl-dC) was assayed at about 1.89 µM (0.15 µg/100 µL) and the methyl donor S-adenosyl-L-[methyl $^3$H]methionine (SAM) was assayed at 0.9 µM (0.5µCi/reaction). The reaction was incubated at 37° C. for 90 minutes and the methylated poly (dl-dC):(dl-dC) product was collected on DEAE filters. After drying, the amount of product bound to the filters could be determined by scintilation counting.

What is claimed is:

1. Indolyl-2-phenyl bisamidines comprising a compound of Formula (1.0.1):

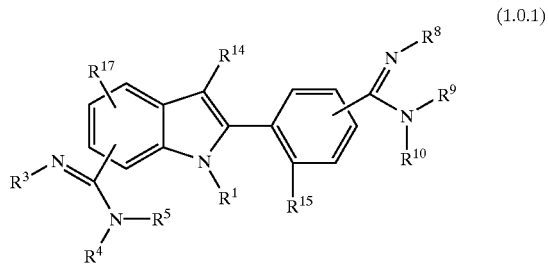

(1.0.1)

or a pharmaceutically acceptable salt thereof, wherein:
$R^1$ is $(C_1-C_3)$alkyl;
$R^3$, $R^4$, $R^5$, $R^8$, $R^9$, and $R^{10}$ are each independently selected from the group consisting of $(C_1-C_3)$alkyl;
— or —
$R^3$ and $R^4$ may be taken together, or $R^8$ and $R^9$ may be taken together with the nitrogen atoms to which they are attached, to form an imidazolinyl group; or further together with an additional ring carbon, —CH$_2$—, to form a 1,4,5,6-tetrahydropyrimidinyl group;
$R^{14}$ is independently selected from the group consisting of —H; —NHC(=O)(CH$_2$)$_m$R$^{20}$; —(CH$_2$)$_m$R$^{20}$; —CH(CH$_3$)R$^{20}$; (CH$_2$)$_m$(C$_6$H$_4$)—R$^{17}$; —(CH$_2$)$_m$(C$_6$H$_4$)—R$^{20}$; —(CH$_2$)$_m$(heterocyclyl)—R$^{17}$; —(CH$_2$)$_m$(heterocyclyl)—R$^{20}$; —CH$_2$CH=CHR$^{20}$; —(CH$_2$)$_m$C(=O)NHCHR$^{20}$R$^{21}$; and —(CH$_2$)$_m$C(=O)NH—CH$_2$—C(=O)NHCHR$^{20}$R$^{21}$;
$R^{15}$ is independently selected from the group consisting of hydrogen; —OR$^1$; —O—(C$_1$-C$_3$)alkylenyl-R$^{20}$; and —OR$^{20}$;
$R^{17}$ is independently selected from the group consisting of hydrogen; halogen; (C$_1$-C$_3$)alkyl; —CF$_3$; —CN; —NO$_2$; —N(R$^1$)$_2$; —OH; and (C$_1$-C$_3$) alkyl(C$_1$-C$_3$) alkoxy;
$R^{20}$ is independently selected from the group consisting of —C(=O)OR$^1$; CH(OH)CH$_2$OH; —C(=O)NH$_2$; and —C(=O)H;

$R^{21}$ is independently selected from the group consisting of hydrogen; $(C_1-C_6)$alkyl; —$(CH_2)_nR^{22}$; —CH$(CH_3)CH_2C(=O)OR^1$; and —$CH_2$—$(C_6H_5)$;

$R^{22}$ is independently selected from the group consisting of —H; —$NH_2$; —$OR^1$; —$SR^1$; —CN; —$OCH_2$—$(C_6H_5)$; —$O(CH_2)_m$—$OR^1$; —$C(=O)OR^1$; thienyl; tetrahydropyranyl; —CH(OH)CH$_2$OH; —$C(=O)C(CH_3)=CH_2$; —NHC(=O)OCH$_2$—$(C_6H_5)$; and —$S(=O)_2R^1$;

m is an integer independently selected from 1, 2, and 3;

—and— n is an integer independently selected from 1 through 5, inclusive.

2. A compound according to claim 1 wherein the $R^1$ substituent has the meaning of methyl.

3. A compound according to claim 1 wherein the carbamimidoyl groups of Formula (1.0.1) are attached thereto so as to result in the configuration of partial Formula (1.3.1):

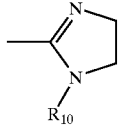

(1.3.1)

where the symbol "*" indicates the points of attachment of the substituents $R^3$, $R^4$, $R^5$, $R^8$, $R^9$, and $R^{10}$, which are not shown.

4. Indolyl-2-phenyl bisamidines comprising a compound of Formula (1.0.1):

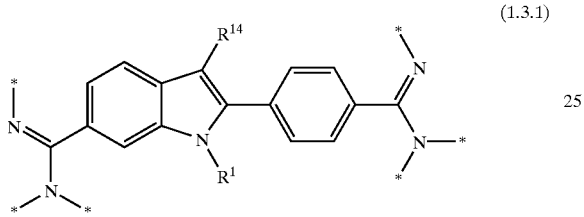

(1.0.1)

or a pharmaceutically acceptable salt thereof, wherein:

$R^1$ is independently selected from the group consisting of hydrogen; and $(C_1-C_3)$alkyl;

$R^3$ and $R^4$ are taken together, and $R^8$ and $R^9$ are taken together, with the nitrogen atoms to which they are attached, to form imidazolinyl groups of partial Formulas (1.5.1) and (1.5.2):

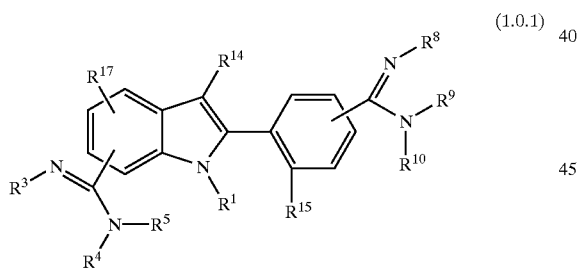

(1.5.1)

(1.5.2)

where $R^5$ and $R^{10}$ are each independently selected from the group consisting of hydrogen; and $(C_1-C_3)$alkyl;

$R^{14}$ is independently selected from the group consisting of —H; —NHC(=O)$(CH_2)_mR^{20}$; —$(CH_2)_mR^{20}$; —CH$(CH_3)R^{20}$; —$(CH_2)_m(C_6H_4)$—$R^{17}$; —$(CH_2)_m(C_6H_4)$—$R^{20}$; —$(CH_2)_m$(heterocyclyl)—$R^{17}$; —$(CH_2)_m$(heterocyclyl)—$R^{20}$; —$CH_2CH=CHR^{20}$; —$(CH_2)_mC(=O)NHCHR^{20}R^{21}$; and —$(CH_2)_mC(=O)NH$—$CH_2$—$C(=O)NHCHR^{20}R^{21}$;

$R^{15}$ is independently selected from the group consisting of hydrogen; —$OR^1$; —O—$(C_1-C_3)$alkylenyl-$R^{20}$; and —$OR^{20}$;

$R^{17}$ is independently selected from the group consisting of hydrogen; halogen; $(C_1-C_3)$alkyl; —$CF_3$; —CN; —$NO_2$; —$N(R^1)_2$; —OH; and $(C_1-C_3)$alkyl$(C_1-C_3)$alkoxy;

$R^{20}$ is independently selected from the group consisting of —$C(=O)OR^1$; $CH(OH)CH_2OH$; —$C(=O)NH_2$; and —$C(=O)H$;

$R^{21}$ is independently selected from the group consisting of hydrogen; $(C_1-C_6)$alkyl; —$(CH_2)_nR^{22}$; —CH$(CH_3)CH_2C(=O)OR^1$; and —$CH_2$—$(C_6H_5)$;

$R^{22}$ is independently selected from the group consisting of —H; —$NH_2$; —$OR^1$; —$SR^1$; —CN; —$OCH_2$—$(C_6H_5)$; —$O(CH_2)_m$—$OR^1$; —$C(=O)OR^1$; thienyl; tetrahydropyranyl; —CH(OH)CH$_2$OH; —$C(=O)C(CH_3)=CH_2$; —NHC(=O)OCH$_2$—$(C_6H_5)$; and —$S(=O)_2R^1$;

m is an integer independently selected from 1, 2, and 3;

—and— n is an integer independently selected from 1 through 5, inclusive.

5. Indolyl-2-phenyl bisamidines comprising a compound of Formula (1.0.1):

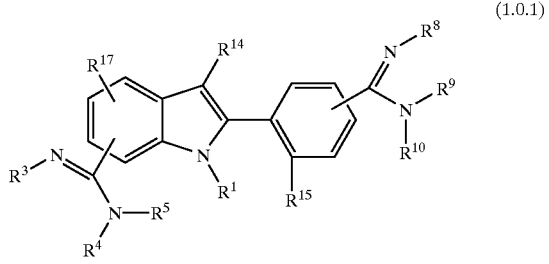

(1.0.1)

or a pharmaceutically acceptable salt thereof, wherein:

$R^1$ is independently selected from the group consisting of hydrogen; and $(C_1-C_3)$alkyl;

$R^3$, $R^4$, $R^5$, $R^8$, $R^9$, and $R^{10}$ are each independently selected from the group consisting of hydrogen; and $(C_1-C_3)$alkyl;

— or —

$R^3$ and $R^4$ may be taken together, or $R^8$ and $R^9$ may be taken together with the nitrogen atoms to which they are attached, to form an imidazolinyl group; or further together with an additional ring carbon, —$CH_2$—, to form a 1,4,5,6-tetrahydropyrimidinyl group;

R$^{14}$ is independently selected from the group consisting of; —NHC(=O)(CH$_2$)$_m$R$^{20}$; —(CH$_2$)$_m$R$^{20}$; —CH(CH$_3$)R$^{20}$; —(CH$_2$)$_m$(C$_6$H$_4$)—R$^{17}$; —(CH$_2$)$_m$(C$_6$H$_4$)—R$^{20}$; —(CH$_2$)$_m$(heterocyclyl)—R$^{17}$; —(CH$_2$)$_m$(heterocyclyl)—R$^{20}$; —CH$_2$CH=CHR$^{20}$; —(CH$_2$)$_m$C(=O)NHCHR$^{20}$R$^{21}$; and —(CH$_2$)$_m$C(=O)NH—CH$_2$—C(=O)NHCHR$^{20}$R$^{21}$;

R$^{15}$ is independently selected from the group consisting of hydrogen; —OR$^1$; —O—(C$_1$–C$_3$)alkylenyl-R$^{20}$; and —OR$^{20}$;

R$^{17}$ is independently selected from the group consisting of hydrogen; halogen; (C$_1$–C$_3$)alkyl; —CF$_3$; —CN; —NO$_2$; —N(R$^1$)$_2$; —OH; and (C$_1$–C$_3$) alkyl(C$_1$–C$_3$) alkoxy;

R$^{20}$ is independently selected from the group consisting of —C(=O)OR$^1$; CH(OH)CH$_2$OH; —C(=O)NH$_2$; and —C(=O)H;

R$^{21}$ is independently selected from the group consisting of hydrogen; (C$_1$–C$_6$)alkyl; —(CH$_2$)$_n$R$^{22}$; —CH(CH$_3$)CH$_2$C(=O)OR$^1$; and —CH$_2$—(C$_6$H$_5$);

R$^{22}$ is independently selected from the group consisting of —H; —NH$_2$; —OR$^1$; —SR$^1$; —CN; —OCH$_2$—(C$_6$H$_5$); —O(CH$_2$)$_m$—OR$^1$; —C(=O)OR$^1$; thienyl; tetrahydropyranyl; —CH(OH)CH$_2$OH; —C(=O)C(CH$_3$)=CH$_2$; —NHC(=O)OCH$_2$—(C$_6$H$_5$); and —S(=O)$_2$R$^1$;

m is an integer independently selected from 1, 2, and 3; —and— n is an integer independently selected from 1 through 5, inclusive; wherein the carbamimidoyl groups of Formula (1.0.1) are attached thereto so as to result in the configuration of partial Formula (1.3.1):

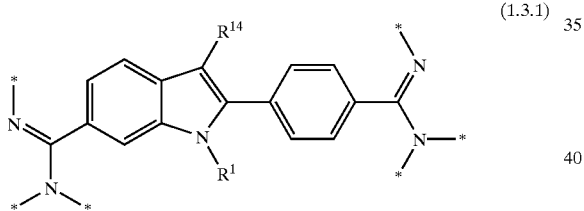

(1.3.1)

where the symbol "*" indicates the points of attachment of the substituents R$^3$, R$^4$, R$^5$, R$^8$, R$^9$, and R$^{10}$, which are not shown.

6. A compound according to claim 5 wherein R$^{17}$ has the meaning hydrogen or halogen; and R$^{20}$ has the meaning —C(=O)OR$^1$ or —C(=O)NH$_2$.

7. A compound according to claim 5, wherein R$^{14}$ has the meaning —NHC(=O)(CH$_2$)$_m$R$^{20}$; —(CH$_2$)$_m$R$^{20}$; —CH(CH$_3$)R$^{20}$; or CH$_2$CH=CHR$^{20}$.

8. A compound according to claim 7, wherein R$^{14}$ has the meaning —(CH$_2$)$_m$C(=O)NHCHR$^{20}$R$^{21}$; or —(CH$_2$)$_m$C(=O)NH—CH$_2$—C(=O)NHCHR$^{20}$R$^{21}$.

9. A compound which is a member independently selected from the group consisting of:

N-Methyl-2-[4-(N-methylcarbamimidoyl)-phenyl]-1H-indole-6-carboxamidine dihydrochloride;

6-(4,5-Dihydro-1H-imidazol-2-yl)-2-[4-(4,5-dihydro-1H-imidazol-2-yl)-phenyl]-5-fluoro-1H-indole dihydrochloride;

2-(4-Carbamimidoyl-2-hydroxy-phenyl)-1H-indole-6-carboxamidine dihydrochloride;

[6-Carbamimidoyl-2-(4-carbamimidoyl-phenyl)-1H-indol-3-yl]-acetic acid dihydrochloride;

2-[4-Carbamimidoyl-2-(2-hydroxy-ethoxy)-phenyl]-1H-indole-6-carboxamidine dihydrochloride;

2-(4-Carbamimidoyl-2-methoxy-phenyl)-1H-indole-6-carboxamidine dihydrochloride;

[6-Carbamimidoyl-2-(4-carbamimidoyl-phenyl)-1H-indol-3-yl]-acetic acid isopropyl ester dihydrochloride;

[6-Carbamimidoyl-2-(4-carbamimidoyl-phenyl)-1H-indol-3-yl]-acetic acid sec-butyl ester dihydrochloride;

2-[5-Carbamimidoyl-2-(6-carbamimidoyl-1H-indol-2-yl)-phenoxy]-propionic acid isopropyl ester dihydrochloride;

2-[4-Carbamimidoyl-2-(2,3-dihydroxy-propoxy)-phenyl]-1H-indole-6-carboxamidine dihydrochloride;

[6-Carbamimidoyl-2-(4-carbamimidoyl-phenyl)-1H-indol-3-yl]-acetic acid butyl ester dihydrochloride;

[6-Carbamimidoyl-2-(4-carbamimidoyl-phenyl)-1H-indol-3-yl]-acetic acid propyl ester dihydrochloride;

2-[6-Carbamimidoyl-2-(4-carbamimidoyl-phenyl)-1H-indol-3-yl]-propionic acid dihydrochloride;

{6-(4,5-Dihydro-1H-imidazol-2-yl)-2-[4-(4,5-dihydro-1H-imidazol-2-yl)-phenyl]-1H-indol-3-yl}-acetic acid dihydrochloride;

{6-(4,5-Dihydro-1H-imidazol-2-yl)-2-[4-(4,5-dihydro-1H-imidazol-2-yl)-phenyl]-1H-indol-3-yl}-acetic acid ethyl ester dihydrochloride;

{6-Carbamimidoyl-2-[4-(4,5-dihydro-1H-imidazol-2-yl)-phenyl]-1H-indol-3-yl}-acetic acid dihydrochloride;

[6-Carbamimidoyl-2-(4-carbamimidoyl-2-methoxy-phenyl)-1H-indol-3-yl]-acetic acid ethyl ester dihydrochloride;

4-[6-Carbamimidoyl-2-(4-carbamimidoyl-phenyl)-1H-indol-3-ylmethyl]-benzoic acid methyl ester dihydrochloride;

2-[6-Carbamimidoyl-2-(4-carbamimidoyl-phenyl)-1H-indol-3-yl]-propionic acid methyl ester dihydrochloride;

5-[6-Carbamimidoyl-2-(4-carbamimidoyl-phenyl)-1H-indol-3-ylmethyl]-furan-2-carboxylic acid methyl ester dihydrochloride;

[6-Carbamimidoyl-2-(4-carbamimidoyl-phenyl)-1H-indol-3-yl]-acetic acid 2-methoxy-ethyl ester dihydrochloride;

[6-Carbamimidoyl-2-(4-carbamimidoyl-phenyl)-1H-indol-3-yl]-acetic acid 2-hydroxy-ethyl ester dihydrochloride;

2-[6-Carbamimidoyl-2-(4-carbamimidoyl-phenyl)-1H-indol-3-ylmethyl]-benzoic acid methyl ester dihydrochloride;

[6-Carbamimidoyl-2-(4-carbamimidoyl-2-hydroxy-phenyl)-1H-indol-3-yl]-acetic acid methyl ester dihydrochloride;

[6-Carbamimidoyl-2-(4-carbamimidoyl-phenyl)-1H-indol-3-yl]-acetic acid allyl ester dihydrochloride;

3-{[6-Carbamimidoyl-2-(4-carbamimidoyl-phenyl)-1H-indol-3-yl]-acetoxy}-butyric acid ethyl ester dihydrochloride;

[6-Carbamimidoyl-2-(4-carbamimidoyl-phenyl)-1H-indol-3-yl]-acetic acid 2-cyano-ethyl ester dihydrochloride;

4-[6-Carbamimidoyl-2-(4-carbamimidoyl-phenyl)-1H-indol-3-yl]-but-2-enoic acid methyl ester dihydrochloride;

2-{3-[6-Carbamimidoyl-2-(4-carbamimidoyl-phenyl)-1H-indol-3-ylmethyl]-phenoxy}-acetamide dihydrochloride;

3-{4-[6-Carbamimidoyl-2-(4-carbamimidoyl-phenyl)-1H-indol-3-ylmethyl]-phenyl}-acrylic acid methyl ester dihydrochloride;

3-[6-Carbamimidoyl-2-(4-carbamimidoyl-phenyl)-1H-indol-3-ylmethyl]-benzoic acid methyl ester dihydrochloride;

[6-Carbamimidoyl-2-(4-carbamimidoyl-phenyl)-1H-indol-3-yl]-acetic acid benzyl ester dihydrochloride;

[6-Carbamimidoyl-2-(4-carbamimidoyl-phenyl)-1H-indol-3-yl]-acetic acid 5-hydroxy-pentyl ester dihydrochloride;

[6-Carbamimidoyl-2-(4-carbamimidoyl-phenyl)-1H-indol-3-yl]-acetic acid 2-benzyloxy-ethyl ester dihydrochloride;

2-[6-Carbamimidoyl-2-(4-carbamimidoyl-phenyl)-1H-indol-3-ylmethyl]-5-chloro-benzoic acid methyl ester dihydrochloride;

{2-[6-Carbamimidoyl-2-(4-carbamimidoyl-phenyl)-1H-indol-3-yl]-ethylamino}-acetic acid dihydrochloride;

{2-[6-Carbamimidoyl-2-(4-carbamimidoyl-phenyl)-1H-indol-3-yl]-ethylamino}-acetic acid methyl ester dihydrochloride;

{2-[6-Carbamimidoyl-2-(4-carbamimidoyl-phenyl)-1H-indol-3-yl]-ethylamino}-acetic acid ethyl ester dihydrochloride;

2-{2-[6-Carbamimidoyl-2-(4-carbamimidoyl-phenyl)-1H-indol-3-yl]-ethylamino}-3-hydroxy-propionic acid methyl ester dihydrochloride;

2-{2-[6-Carbamimidoyl-2-(4-carbamimidoyl-phenyl)-1H-indol-3-yl]-ethylamino}-succinic acid dimethyl ester dihydrochloride; [6-Carbamimidoyl-2-(4-carbamimidoyl-phenyl)-1H-indol-3-yl]-acetic acid 2-(2-hydroxy-ethoxy)-ethyl ester dihydrochloride;

[6-Carbamimidoyl-2-(4-carbamimidoyl-phenyl)-1H-indol-3-yl]-acetic acid 2-ethylsulfanyl-ethyl ester dihydrochloride;

[6-Carbamimidoyl-2-(4-carbamimidoyl-phenyl)-1H-indol-3-yl]-acetic acid 2-thiophen-2-yl-ethyl ester dihydrochloride;

[6-Carbamimidoyl-2-(4-carbamimidoyl-phenyl)-1H-indol-3-yl]-acetic acid tetrahydro-pyran-2-ylmethyl ester dihydrochloride;

[6-Carbamimidoyl-2-(4-carbamimidoyl-phenyl)-1H-indol-3-yl]-acetic acid 2-(2-methoxy-ethoxy)-ethyl ester dihydrochloride;

[6-Carbamimidoyl-2-(4-carbamimidoyl-phenyl)-1H-indol-3-yl]-acetic acid 2,3-dihydroxy-propyl ester dihydrochloride;

2-Methyl-acrylic acid 2-{[6-carbamimidoyl-2-(4-carbamimidoyl-phenyl)-1H-indol-3-yl]-acetoxy}-ethyl ester dihydrochloride;

2-{2-[6-Carbamimidoyl-2-(4-carbamimidoyl-phenyl)-1H-indol-3-yl]-ethylamino}-propionic acid methyl ester dihydrochloride;

2-{2-[6-Carbamimidoyl-2-(4-carbamimidoyl-phenyl)-1H-indol-3-yl]-ethylamino}-3-methyl-acid methyl ester dihydrochloride;

2-{2-[6-Carbamimidoyl-2-(4-carbamimidoyl-phenyl)-1H-indol-3-yl]-ethylamino}-3-phenyl-acid methyl ester dihydrochloride;

[6-Carbamimidoyl-2-(4-carbamimidoyl-phenyl)-1H-indol-3-yl]-acetic acid 2-(butane-1-sulfonyl)-ethyl ester dihydrochloride;

3-{2-[6-Carbamimidoyl-2-(4-carbamimidoyl-phenyl)-1H-indol-3-yl]-ethylamino}-propionic acid methyl ester dihydrochloride;

2-(4-Carbamimidoyl-phenyl)-3-(2,3-dihydroxy-propyl)-1H-indole-6-carboxamidine dihydrochloride;

{6-(4,5-Dihydro-1H-imidazol-2-yl)-2-[4-(4,5-dihydro-1H-imidazol-2-yl)-phenyl]-1H-indol-3}-acetaldehyde dihydrochloride;

N-[6-Carbamimidoyl-2-(4-carbamimidoyl-phenyl)-1H-indol-3-yl]-succinamic acid dihydrochloride;

5-Benzyloxycarbonylamino-2-{2-[6-carbamimidoyl-2-(4-carbamimidoyl-phenyl)-1H-indol-3-yl]-acetylamino}-pentanoic acid methyl ester dihydrochloride;

5-Amino-2-{2-[6-carbamimidoyl-2-(4-carbamimidoyl-phenyl)-1H-indol-3-yl]-acetylamino}-pentanoic acid methyl ester dihydrochloride;

2-(2-{2-[6-Carbamimidoyl-2-(4-carbamimidoyl-phenyl)-1H-indol-3-yl]-acetylamino}-acetyl pentanedioic acid dibenzyl ester dihydrochloride;

—and—

6-Amino-2-{2-[6-carbamimidoyl-2-(4-carbamimidoyl-phenyl)-1H-indol-3-yl]-acetylamino}-hexanoic acid methyl ester dihydrochloride.

10. A pharmaceutical composition for use as an antiproliferative agent, comprising a therapeutically effective amount of an indolyl-2-phenyl bisamidine compound of Formula (1.0.1) as defined in any one of claims 1,4,5, or 7 together with a pharmaceutically acceptable carrier for said compound.

11. A method of treating a neoplastic disease that is a member independently selected from the group consisting of melanoma, colon cancer; bladder cancer, non-small cell lung cancer, gliomas, head and neck squamous cell carcinoma, breast cancer, prostate cancer, renal cancer, and nasopharyngeal carcinoma; and that is further characterized by abnormally rapid proliferation of tissue involved in said disease which is mediated by or associated with abnormally increased levels of DNA methylation, comprising administering to a patient in need of such treatment a therapeutically effective amount of a compound of Formula (1.0.1) as defined in any one of claims 1, 4, 5 or 9.

12. A method according to claim 11 wherein said patient is a human.

* * * * *